United States Patent
Micic et al.

(10) Patent No.: US 11,326,987 B2
(45) Date of Patent: May 10, 2022

(54) CULTIVATION AND SAMPLING METHOD

(71) Applicant: Deutsche Saatveredelung AG, Lippstadt (DE)

(72) Inventors: Zeljko Micic, Salzkotten (DE); Simon Radtke, Soest (DE)

(73) Assignee: DEUTSCHE SAATVEREDELUNG AG, Lippstadt (DE)

( * ) Notice: Subject to any disclaimer, the term of this patent is extended or adjusted under 35 U.S.C. 154(b) by 636 days.

(21) Appl. No.: 16/293,097

(22) Filed: Mar. 5, 2019

(65) Prior Publication Data

US 2019/0195746 A1    Jun. 27, 2019

Related U.S. Application Data

(63) Continuation of application No. PCT/DE2017/100740, filed on Sep. 5, 2017.

(30) Foreign Application Priority Data

Sep. 5, 2016 (EP) .................................. 16187274

(51) Int. Cl.
| | |
|---|---|
| *G01N 1/04* | (2006.01) |
| *A01G 9/029* | (2018.01) |
| *A01G 31/06* | (2006.01) |
| *A01G 7/00* | (2006.01) |
| *G01N 33/00* | (2006.01) |

(Continued)

(52) U.S. Cl.
CPC ................. *G01N 1/04* (2013.01); *A01G 3/00* (2013.01); *A01G 7/00* (2013.01); *A01G 9/028* (2013.01); *A01G 9/029* (2018.02); *A01G 31/06* (2013.01); *G01N 1/286* (2013.01); *G01N 33/0098* (2013.01); *A01G 31/02* (2013.01); *G01N 1/00* (2013.01); *G01N 2001/288* (2013.01); *G01N 2001/2873* (2013.01)

(58) Field of Classification Search
None
See application file for complete search history.

(56) References Cited

U.S. PATENT DOCUMENTS

| 8,758,683 B2 | 6/2014 | Lafferty et al. |
| 2013/0180171 A1 | 7/2013 | Oldenburg |
| 2014/0374518 A1 | 12/2014 | Chen |

FOREIGN PATENT DOCUMENTS

| JP | 2008118963 A | 5/2008 |
| WO | WO2009020766 A1 | 2/2009 |

(Continued)

OTHER PUBLICATIONS

International Search Report dated Jan. 5, 2018 in corresponding application PCT/DE2017/100740.

(Continued)

*Primary Examiner* — Daniel S Larkin
(74) *Attorney, Agent, or Firm* — Muncy, Geissler, Olds & Lowe, P.C.

(57) ABSTRACT

A cultivation and sampling method for plants grown in a multi-section sampling device, the sampling device including an upper section with an upper section identifier and a number of cultivation containers, and a lower section with a lower section identifier and an equal number of sample containers. When the sampling device is in an assembled position, the upper section is connected to the lower section such that the sample containers are arranged to correspond to the cultivation containers being underneath them.

14 Claims, 24 Drawing Sheets

(51) Int. Cl.
*A01G 3/00* (2006.01)
*A01G 9/02* (2018.01)
*G01N 1/28* (2006.01)
 A01G 31/02 (2006.01)
 G01N 1/00 (2006.01)

(56) References Cited

FOREIGN PATENT DOCUMENTS

WO  WO2012096568 A1  7/2012
WO  WO2013104801 A1  7/2013

OTHER PUBLICATIONS

International Preliminary Report on Patentability dated Mar. 5, 2019 in corresponding application PCT/DE2017/100740.

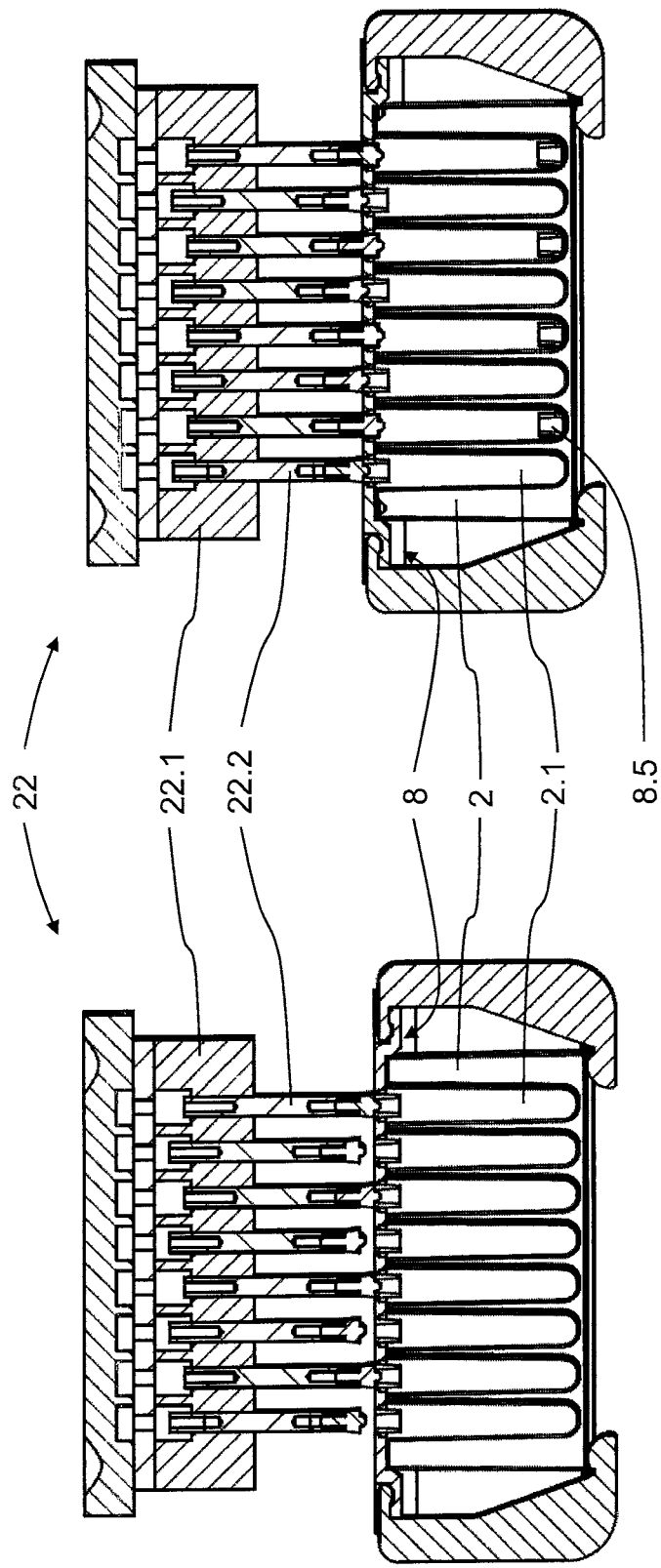

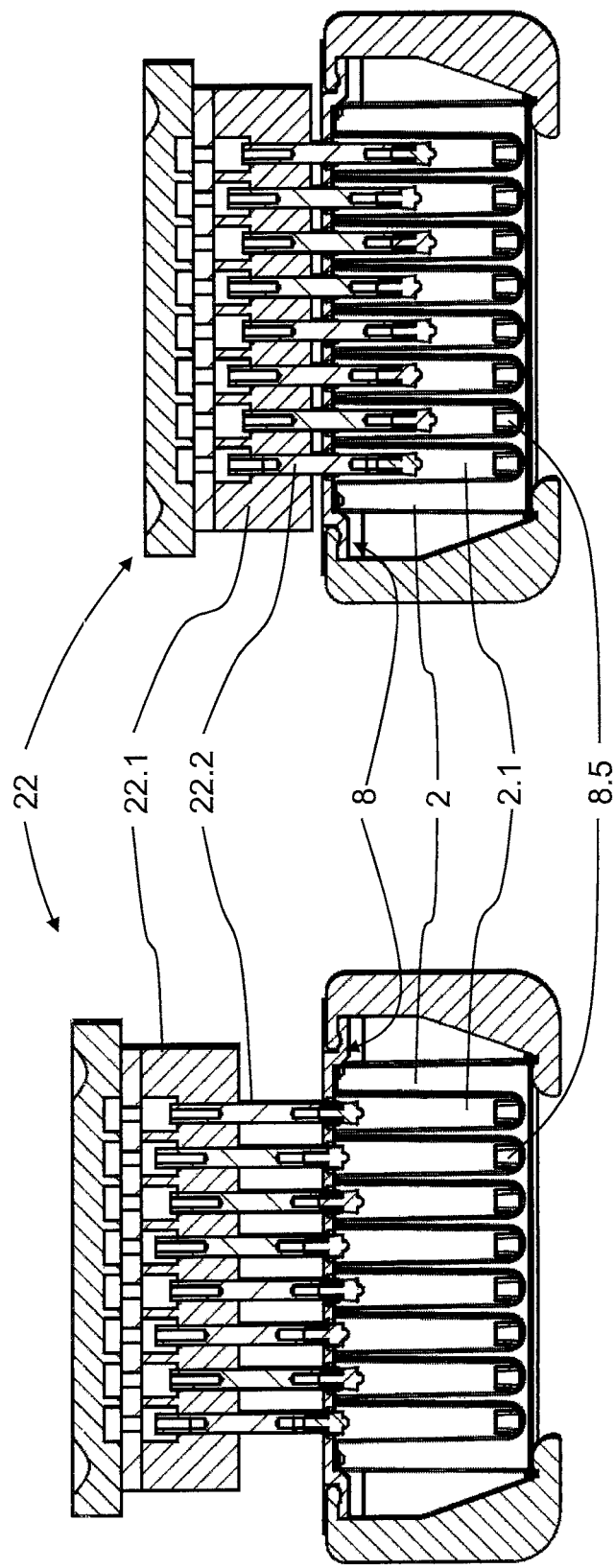

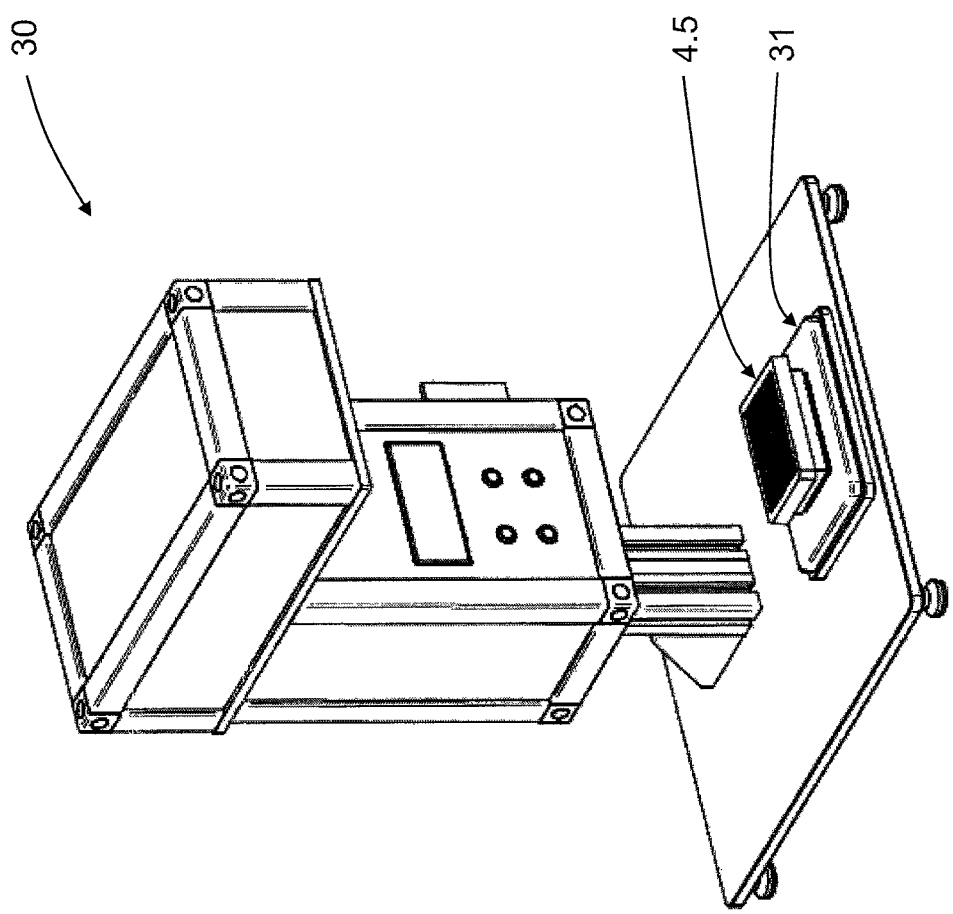

CULTIVATION AND SAMPLING METHOD

This nonprovisional application is a continuation of International Application No. PCT/DE2017/100740, which was filed on Sep. 5, 2017, and which claims priority to European Patent Application No. 16 187 274.2, which was filed on Sep. 5, 2016, and which are both herein incorporated by reference.

BACKGROUND OF THE INVENTION

Field of the Invention

The present invention relates to a cultivation and sampling method for plants. In this context, the plants are grown in cultivation containers. Then, samples are taken from the plants for phenotypic description and/or molecular biological testing. After analyzing the samples, the plants which are particularly suitable according to a given specification are selected and used for further cultivation.

Description of the Background Art

Cultivation and sampling methods have been known and used in practice for many years. Usually, the sampling takes place manually with the help of tongs and/or punching tools with which tissue is punched out of the plants grown. The punched out plant parts, such as chlorophyll, are then placed in sample containers and submitted for further testing. The process is very labor-intensive and time-consuming, since large quantities of plants have to be grown, analyzed and selected in a multistage development process until finally a plant with the desired properties can be provided. In particular due to a very high proportion of manual work, the method is fundamentally susceptible to error.

For example, it can happen that samples are mixed up or a sample is incorrectly associated with a plant. In addition, there is considerable risk that samples from different plants may be undesirably intermixed and the analysis results are erroneously assigned to a plant.

Also, in the context of the so-called ice-cap method, the use of a multi-part sampling device for a generic cultivation and sampling method is known. In this case, plants are grown from a seed in an upper section of the sampling device. During cultivation, parts of the roots grow into the region of a lower section of the sampling device. In order to separate the root parts grown in the lower section from the rest of the plant in preparation for laboratory testing of the plants, the lower section of the sampling device with the root parts provided therein is flooded and subsequently, the sampling device is frozen. After freezing, the lower section can be separated from the upper section. The root parts frozen in the lower section are removed and examined after thawing. The disadvantage here is that the plants are exposed to increased stress as a result of freezing and, in particular, it is not ensured that the upper section of the plants with the roots remaining in the upper section of the sampling device, once frozen, remain vital. Thus, it is possible that it may not be used to further develop the plant. In addition, the outlay required in terms of the device to freeze the sampling device is relatively high and the implementation of the method is time-consuming.

SUMMARY OF THE INVENTION

It is therefore an object of the present invention to provide an improved cultivation and sampling method for plants.

According to the inventive cultivation and sampling method, the plants are grown in a multi-section sampling device, which on the one hand provides an upper section with an upper section identifier and a number of cultivation containers, and on the other hand, a lower section with a lower section identifier and a number of sample containers. In an assembly position of the sampling device, the upper section is connected to the lower section in such a way that the sample containers corresponding to the cultivation containers are arranged below the same. During a cultivation phase in which the sampling device is in the assembly position, the plants are grown in the cultivation containers. The cultivation containers are filled with a substrate and/or nutrients. After the roots of the plants have grown through a bottom opening provided on each cultivation container into the sample container provided below the cultivation container, the root parts provided in the lower section are separated from the plant with a cutter. Then, in an analysis phase, the lower section of the sampling device with the root parts located therein is fed to an analysis device. The lower section identifier of the sampling device is recorded and a phenotypic description and/or molecular biological testing is carried out for the different root parts. Then, in a selection phase, the upper section of the sampling device with the plants therein is fed to a selection device. The upper section is positioned and the upper section identifier is recorded.

Advantageously, the phenotypic description and/or the molecular biological testing of the plants is significantly simplified by the inventive method for cultivation and sampling. In particular, manual, individual sampling on the plant leaves by means of tongs and/or a punching tool is avoided and instead, molecular biological testing of the root parts is carried out. The root parts of multiple plants can be cut off together. These are provided directly in the sample containers of the lower section and can undergo analysis without further manual intervention.

The inventive method is also very gentle. For example, it is not necessary to flood or freeze the sampling device having the plants. Thus, the plants in the upper section remain vital and they can be used in a very simple manner for further cultivation. In addition, sampling can be done very quickly.

In addition, due to the reduction of manual work steps and in particular the omission of manual sampling and the manual placement of the samples in the cultivation containers prevents susceptibility to errors.

For reasons of clarity, comprehensibility and simplicity, in the following description, the term "plant" will be uniformly used for the plant as a whole, that is to say the plant with the roots grown into the lower section, as well as for the living remainder of the plant remaining after cutting the roots in the upper section of the sampling device.

The root parts of the plants that have grown into the lower section are separated from the plants by means of a cutter formed as part of the sampling device and, in the assembly position, held on the lower section and/or the upper section. In particular, it can be provided that the root parts are separated from the plants by the cutter being guided along a cutting plate of the sampling device fixed to the lower section. Advantageously, the separation of the root parts can be simplified and the cultivation and sampling method can be further accelerated by realizing the cutter as part of the sampling device. In addition, the integration of the cutter and/or the provision of the cutting plate always results in an identical, exact cutting position with the result that the starting conditions for the subsequent analysis are always the same and reproducible to a high degree. For this purpose, it can be provided, in particular, that the cutter and/or the cutting plate, which are each configured as part of the sampling device, are positioned between the upper section and the lower section of the sampling device.

In the assembly position of the sampling device, sample container openings of the sample containers facing the cultivation containers with the bottom openings can be covered by the cutting plate. The cutting plate in this case provides a number of cutting holes as passage openings for the roots of the plants, which are arranged corresponding to the position of the bottom openings and the sample container openings. Advantageously, the sample container openings being covered by the cutting plate effectively guards against undesirable contamination of the samples.

The cutting plate insofar prevents the roots of a plant from growing in a different sample container other than the one provided underneath the associated cultivation container. Therefore, the cutting plate serves a dual purpose in respect of the inventive cultivation and sampling method. On the one hand, it serves to guide the cutter and thus ensures that the sample taken is always the same, i.e. that the roots are cut at a defined location. On the other hand, it serves to improve analysis by counteracting contamination.

The cutter provided between the upper section and the lower section of the sampling device can be designed in the manner of a perforated cutter plate with a number of cutting holes, which are formed as passage openings and are arranged during the cultivation phase to correspond with the passage openings of the cutting plate in such a way, that the roots can grow into the sample containers. To cut through the roots, the cutter is guided along the cutting plate by a predetermined stroke. The stroke is chosen such that, on the one hand, the roots are reliably severed and, on the other hand, each passage opening formed on the perforated insert of the cutter interacts only with one passage opening in the cutting plate. Insofar, the stroke is chosen to be larger than the diameter of the passage openings provided on the cutting plate and the cutter, and chosen to be smaller than a distance of two sample containers adjacent in the stroke direction. In this way, an undesired mixing (contamination) of the samples is effectively counteracted.

After cutting the roots in preparation for analysis, the lower section of the sampling device with the root parts provided therein can be severed together with the cutting plate from the upper section of the sampling device.

The lower section with the root parts provided therein can be drained. The draining can for example be carried out in that the lower section together with the cutting plate is placed in a centrifugal device and the water is ejected or exits through the passage openings provided on the cutting plate under the influence of the centrifugal force. Due to their material consistency and the small size of the passage openings, the root parts remain in the sample containers of the lower section. Advantageously, further testing of the root parts is facilitated by the removal of the water. By using the centrifugal device, draining can be done quickly and easily. For example, in a further method step, it can be provided that the root parts provided in the lower section are moved to the bottom of the sample containers by means of the centrifugal force. For this purpose, the lower section with the cutting plate and the root parts provided in the lower section can be rotated in the centrifugal device and/or the direction of rotation of the centrifugal device can be changed.

After severing the roots and/or the draining, the lower section with the root parts provided therein and the cutting plate may be supplied to a punching device. By means of a punch of the punching device, annular, preferably circular sections are then punched out of the punching plate around the cutting holes and are transferred into the interior of the respectively assigned sample containers. Advantageously, the risk of contamination of the samples can be further reduced by punching the annular sections. In particular, the separated root parts of the plants, which are still partly in the passage openings of the cutting plate after cutting, are transferred together with the section into the sample container. After punching, therefore, the cutting plate can be removed from the lower section without the risk that root parts adhering to the cutting plate are pulled from the sample containers upon removal of the cutting plate, or that the samples are contaminated. The cutting plate of the sampling device is in particular removed from the lower section before the lower section is supplied to the analysis device for carrying out the phenotypic description and/or molecular biological testing of the samples.

Before punching out the sections from the cutting plate, a positioning head provided on the punches on a free end facing the cutting plate can be brought into engagement with the cutting holes of the cutting plate. Advantageously, by providing the positioning heads and the engagement thereof in the cutting holes of the cutting plate, the cutting plate with the lower section is positioned for the punching device of the sample containers, and a mixing or contamination of the samples is thereby prevented.

A cultivation container of the upper section of the sampling device positioned in the selection device can be identified by a signaler of the selection device. Parts of the plant or the entire plant from the identified cultivation container can then be removed for further cultivation or processing. Advantageously, identifying the cultivation container can counteract faulty removal. The cultivation and sampling method according to the invention can thus be carried out very reliably.

The removal of the selected plants or a part thereof can be automated or semi-automated by means of a gripper of the selection device, which is first positioned for a selected cultivation container and then carries out the removal for the same cultivation container. Advantageously, the selection can be accelerated by the automation. In addition, erroneous removal is prevented.

According to a development of the invention, in the selection phase, a plurality of cultivation containers of a same upper section of the sampling device are sequentially identified by means of the signaler of the selection device. Advantageously, by the sequential identification of the cultivation containers of the same upper section, a mix-up of the samples can be effectively prevented. In this respect, a technical employee can at any time focus on a single cultivation container or a single plant provided therein.

According to a development of the invention, the sampling device can be illuminated during the cultivation phase by means of light emitting diodes. It has been shown that by illuminating the plants during the cultivation phase, the growth of the roots can be accelerated, while at the same time inhibiting longitudinal growth of the shoot. Here, the light intensity and the composition of the light spectrum play a role. For example, visible light in the wavelength range of 400 nm to 700 nm is used. In this case, a lighting device is in particular designed such that the light is emitted, for example, fully spectrally, that is to say over the entire wavelength range, and/or that the blue range (approximately 400 nm to 500 nm), the green-yellow range (approximately 500 nm to 600 nm) and the red range (approximately 600 nm to 700 nm) can be separately activated and/or dimmed. Specifically, it can be provided that individually adapted illumination parameters are used for different cultivars and/or that in each case individual sub ranges of defined size and shape are illuminated homogeneously and with a defined illuminance or spectral composition, taking account of wall reflections and/or overlay effects.

The lighting device may provide a device for cooling the LEDs. For example, it is possible to provide active cooling, in particular water or fluid cooling, in order to be able to discharge the waste heat quickly and in a controlled manner. Alternatively, passive convection cooling can be provided for the light emitting diodes. For example, by means of the waste heat, the cultivation environment can be heated or temperature controlled. In particular, the shelves on which a large number of sampling devices are set up during cultivation can be tempered in a specified manner. The cultivation containers can be filled with a granulate, such as brick grit, as a substrate and/or with nutrients. The cultivation containers are watered during the cultivation phase from above. For this purpose, for example, spray nozzles are used, which are moved over the plants for watering by means of a computer controlled system. For example, after watering, the spray nozzles are brought out of engagement and positioned such that the plants can be illuminated without creating shade. Advantageously, by using brick grits and by irrigating the cultivation containers from above, maintenance can be reduced during the cultivation phase. In addition, unlike with the ice-cap method, there is no need to place the sampling device in a pool of water, to flood this at least partially and to realize a constant water level by means of a pump in the pool. Thus, the cultivation and sampling method is significantly simplified both in terms of handling and in terms of the devices that need to be provided.

Sowing can be done in a signal supported manner such that a sowing device scans in a seed identifier provided on an outer packaging of the seeds of the plants, and by means of a signaler of the sowing device, a selected cultivation container of the sampling device is identified for carrying out the sowing. Advantageously, the cultivation and sampling method is further simplified since already during sowing, a correlation is produced between a plant or the seed of this plant on the one hand, and the cultivation container of the sampling device on the other hand. Mix-ups, for example a faulty listing of the cultivation container or the seed and/or an incorrect assignment of the same, are avoided.

The sowing can be supported mechanically in that the seed is picked up by a gripper of the sowing device and after being positioned by the gripper, is provided in a selected cultivation container of the sampling device. Advantageously, as a result, the cultivation and sampling method according to the invention can be further accelerated. In addition, errors and mix-ups are counteracted by the automation.

The analysis device and/or a separating device actuating the cutter of the sampling device and/or the selection device and/or the sowing device and/or the punching device can be coupled in terms of control technology and/or data technology in such a way that the upper section identifier and/or the lower section identifier and/or the seed identifier are recorded and linked to the analysis results of the molecular biological testing and/or the phenotypic description of the root parts. The results, the identifiers and the assignment can be stored, for example, in a database. For this purpose, for example, the upper section identifier and/or the lower section identifier and/or the seed identifier are designed in the manner of a bar code or the like, and means for optical scanning of the identifiers are provided. With regard to the various cultivation and sample containers of the sampling device, identification can be ensured, for example, in a matrix-like arrangement in that the row and the column of the respective containers is detected. In this respect, an unambiguous assignment of the root parts to the sample containers and the associated cultivation containers advantageously takes place, so that a mix-up of the samples or plants is particularly effectively prevented and they can be reliably identified.

The sowing device and the selection device can use a common signaler and/or gripper. For example, the signaler of the selection device or the sowing device optically identifies the cultivation container of the upper section or the sample container of the lower section. A light emitting diode or a light emitting diode array may insofar be provided as a signaler, in which the number and/or arrangement of the light emitting diodes is adapted to the number and arrangement of the cultivation containers of the upper section of the sampling device.

The sample containers of the lower section can be formed in a 96 deep-well plate format. The area requirement for the cultivation of the plants is advantageously reduced by the use of the standardized 96 deep-well plate format by about 90%, with the result that, for example, in the same greenhouse area, significantly more plants can be grown, or the same number of plants can be grown in a greenhouse that is much smaller and less costly to maintain.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 21 illustrates a second step of the punching operation of the same schematic diagram in section;

FIG. 22 illustrates a third step of the punching operation of the same schematic diagram in section;

FIG. 23 illustrates a fourth step of the punching operation of the same schematic diagram in section;

FIG. 24 illustrates a fifth step of the punching operation of the same schematic diagram in section;

FIG. 25 illustrates a signaler of a selection device and/or sowing device used for carrying out the inventive cultivation and sampling method in a first perspective view.

DETAILED DESCRIPTION

Figure 1:
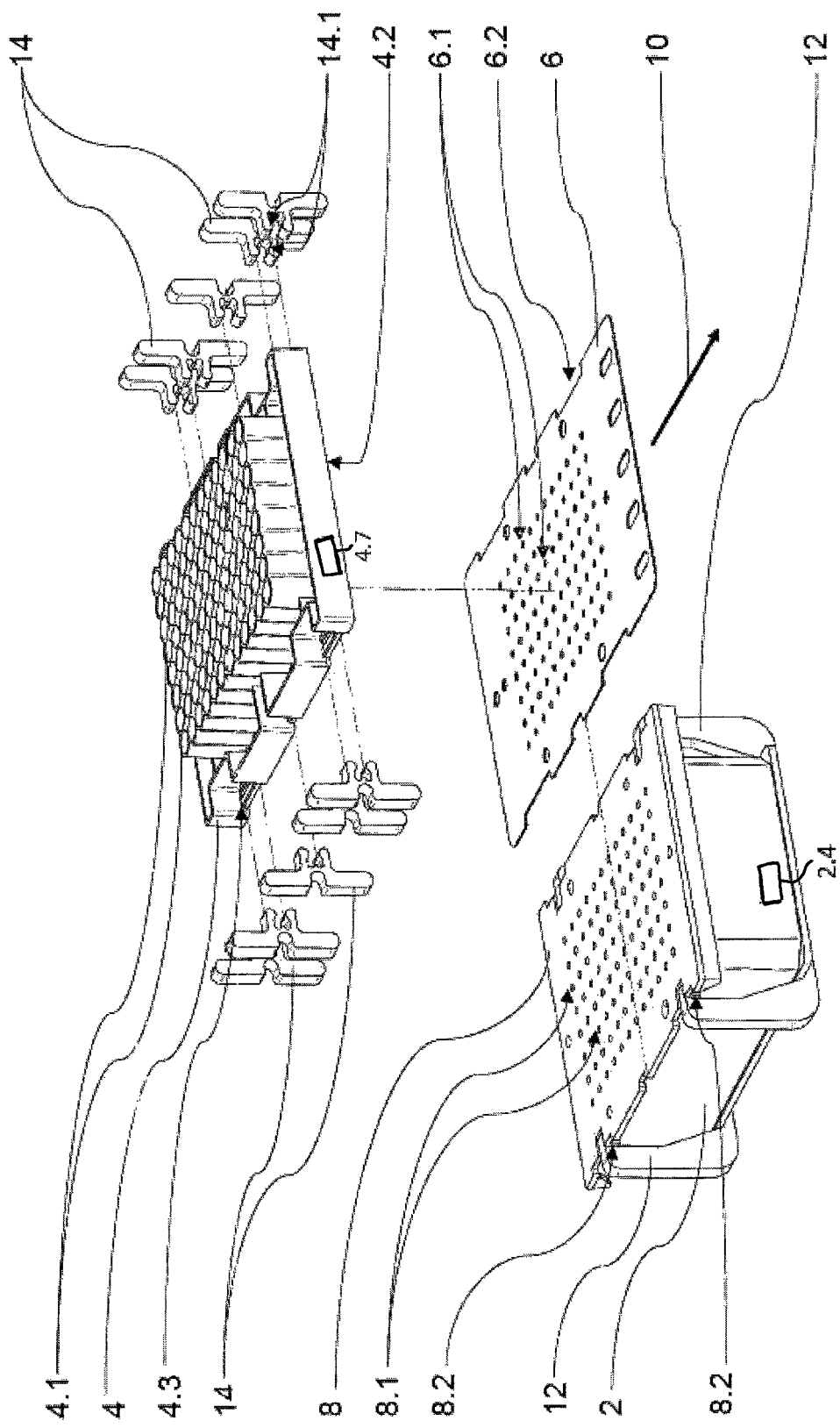
FIG. 1 illustrates an exemplary embodiment of a sampling device used for carrying out the inventive cultivation and sampling method, in a first perspective exploded view.
Figure 2:
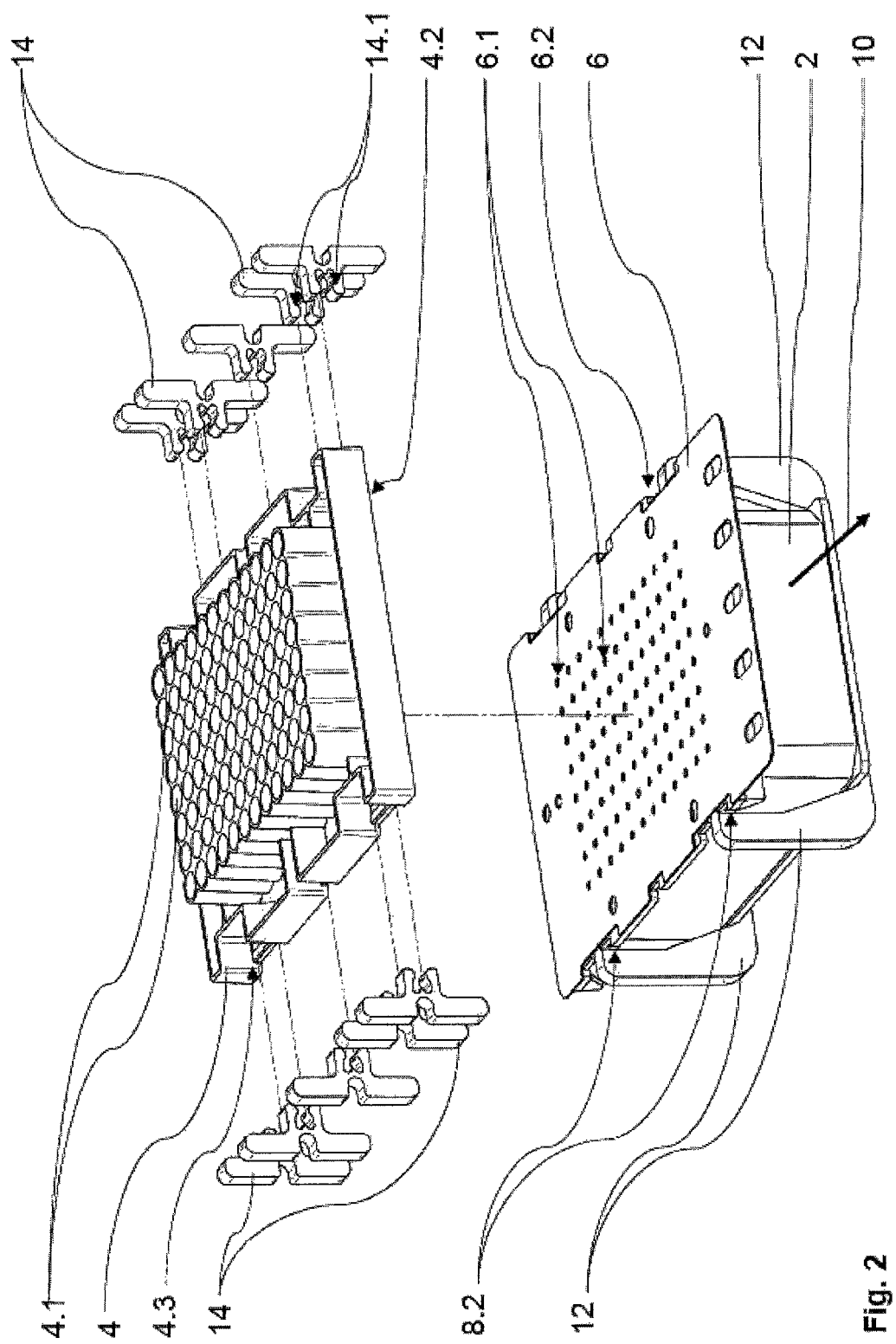
FIG. 2 illustrates the exemplary embodiment of the sampling device in a second perspective exploded view.
Figure 3:
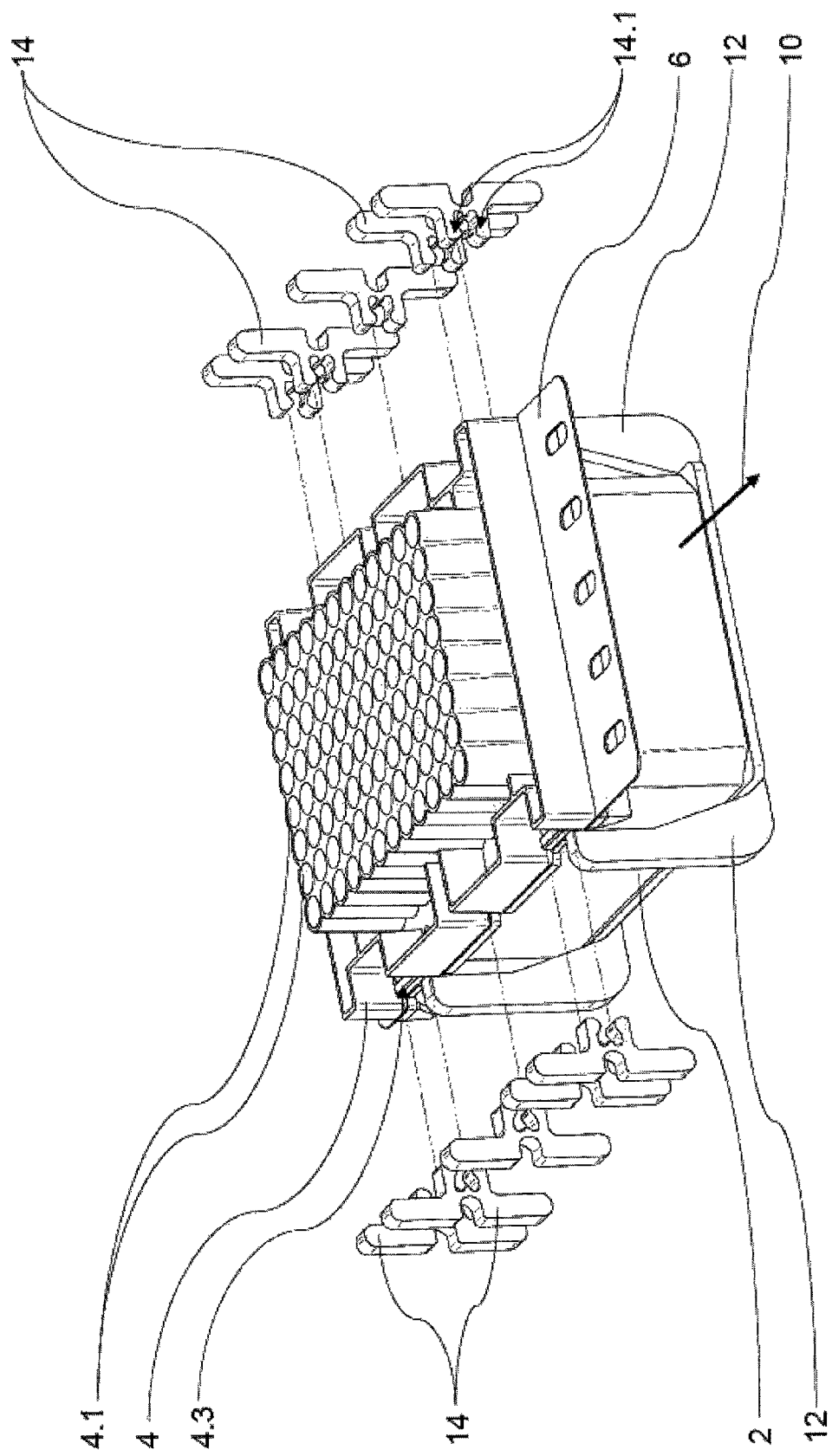
FIG. 3 illustrates the exemplary embodiment of the sampling device in a third perspective exploded view.

FIGS. 1 to 14 show mutually different exemplary embodiments of a sampling device used for carrying out the cultivation and sampling method according to the invention. Further components and functional devices as well as detailed representations for this purpose, which can be used for carrying out the cultivation and sampling method according to the invention, are shown in FIGS. 15 to 26.

The same or identically operating components are uniformly designated with the same reference numerals. Only the features of the exemplary embodiments following the first exemplary embodiment of the sampling device that differ from the first exemplary embodiment will be explained. Otherwise, the exemplary embodiments are identical.

FIG. 1 shows an exemplary embodiment of a sampling device in a perspective exploded view. The sampling device comprises a lower section 2 preferably at least partially made of plastic having a plurality of sample containers 2.1, which are particularly clearly visible in a perspective bottom view of the sampling device of FIG. 5. The sample containers 2.1 are presently realized in a 96 deep-well plate format and arranged in the manner of a 12×8 matrix.

Furthermore, the sampling device has an upper section 4 made of plastic with a plurality of cultivation containers 4.1, a cutter 6 preferably made of plastic or metal and a cutting plate 8 preferably made of plastic. In each cultivation container 4.1, a bottom opening 4.1.1 is formed, which can be seen in FIG. 6. The sample containers 2.1 here are an integral part of the lower section 2, and the cultivation containers 4.1 are an integral part of the upper section 4. In the first exemplary embodiment of the invention, the lower section 2 and the upper section 4 are thus each formed in one piece.

Figure 4:
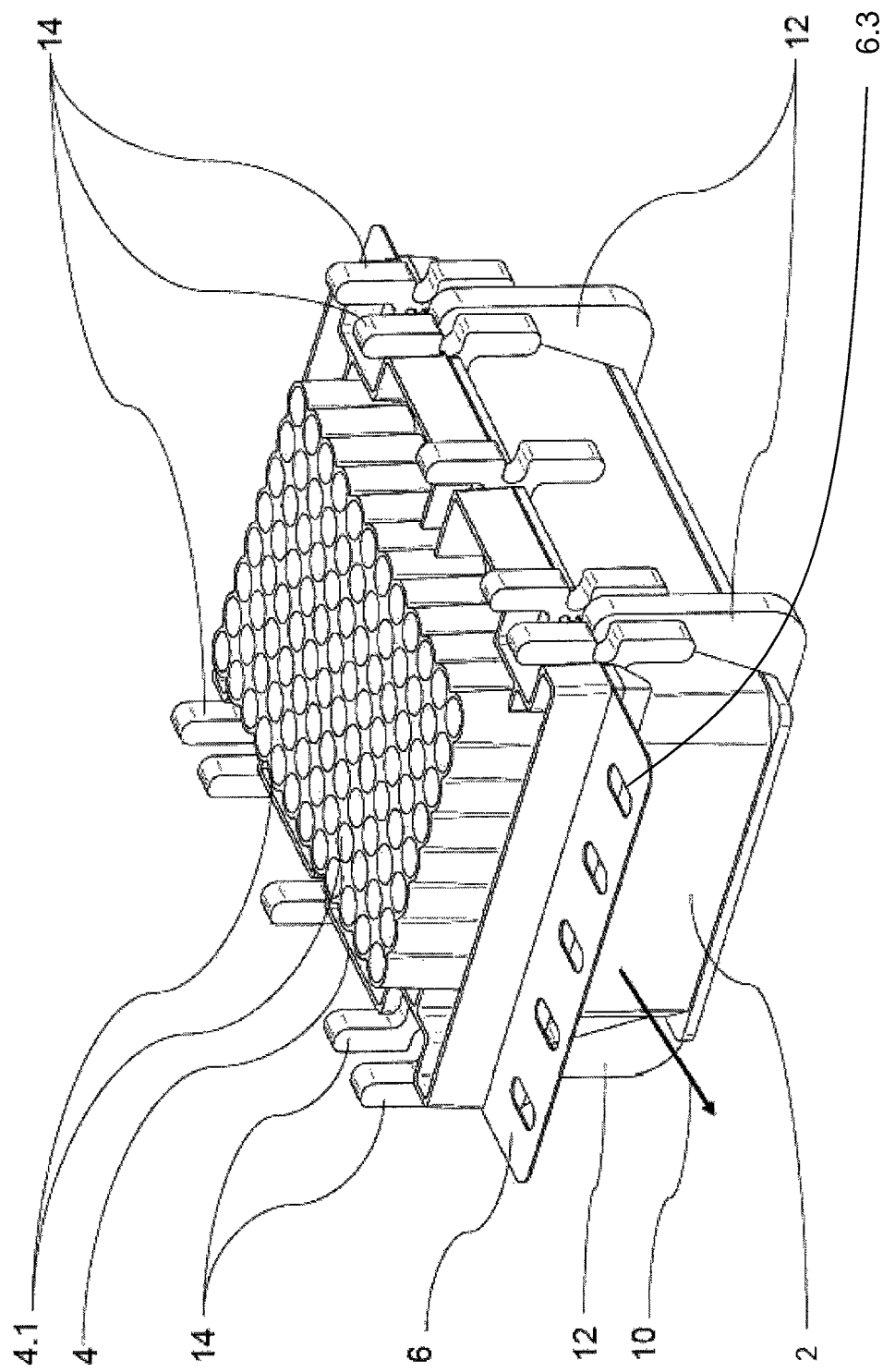
FIG. 4 illustrates the exemplary embodiment of the sampling device in a first perspective assembly view.
Figure 5:
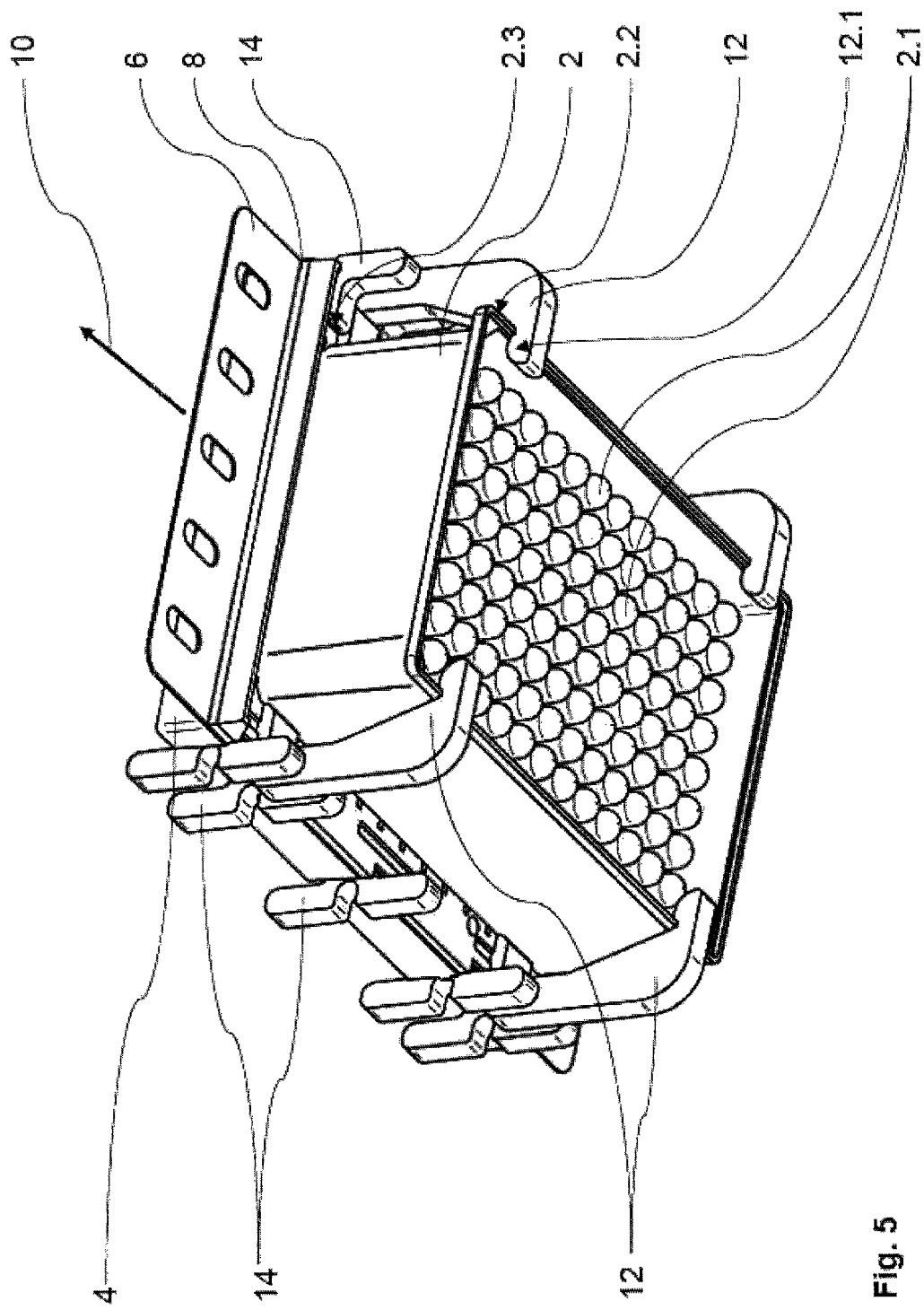
FIG. 5 illustrates the exemplary embodiment of the sampling device in a second perspective assembly view.
Figure 6:
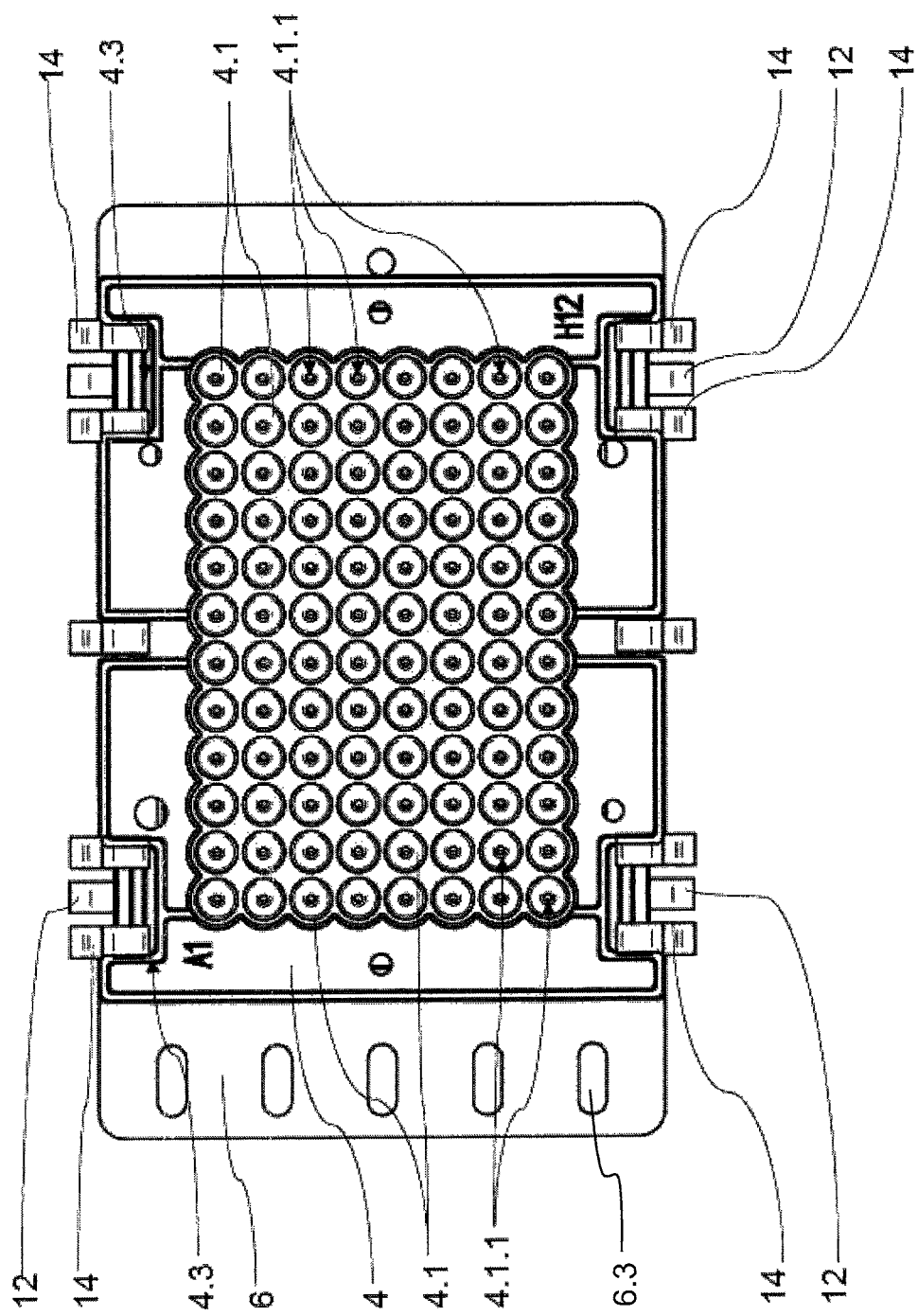
FIG. 6 illustrates the exemplary embodiment of the sampling device in a plan view.

As is clear from the synopsis of the figures, each cultivation container 4.1 is assigned exactly one sample container 2.1 and each bottom opening 4.1.1 is assigned exactly one sample container opening in an assembly position shown in FIGS. 4 to 6. The sample container openings are not explicitly shown since they are covered by the cutting plate 8.

The unambiguous assignment of exactly one cultivation container 4.1 to exactly one sample container 2.1 is useful because the sampling device is provided in particular for the phenotypic description and/or the molecular biological testing of plants. For the success of such tests, it is important that there is no undesirable mixing (cross contamination) of the individual tissue samples (genotypes). This is ensured by the aforementioned configuration of the sampling device.

The cultivation containers 4.1 were initially filled with substrate, not shown, and/or nutrients, for example, brick grit, for plant growth. In the individual cultivation containers 4.1, in each case one plant is grown during use of the sampling device according to the invention. In the course of the plant development, the roots of the plants, not shown, grow through the substrate and the bottom openings 4.1.1 of the cultivation containers 4.1 and the sample container openings into the sample containers 2.1 of the lower section 2 corresponding to the individual cultivation containers 4.1.

In the assembly position of the inventive sampling device shown in FIGS. 4 to 6, the cutter 6 and the cutting plate 8 are arranged such between the upper section 4 and the lower section 2 that the roots projecting out through the bottom openings 4.1.1 of the cultivation containers 4.1 and projecting through the sample container openings into the respective sample container 2.1 can be severed by means of the cutter 6 and the cutting plate 8.

The cutter 6 and the cutting plate 8 are formed here as a perforated cutting plate 6 and a perforated cutting plate 8. The number of cutting holes 6.1, 8.1 formed in the two perforated plates 6, 8 is identical to the number of bottom openings 4.1.1 of the cultivation containers 4.1 and the number of sample container openings of the sample containers 2.1. The cultivation containers 4.1 and the sample containers 2.1 are preferably made of plastic.

In the assembly position shown in FIGS. 4 to 6, the cutting holes 6.1, 8.1 formed on the cutter 6 and the cutting plate 8 are congruent with the bottom openings 4.1.1 and sample container openings corresponding thereto. Accordingly, the roots of the plants grown in the cultivation containers 4.1 can grow unhindered from the respective cultivation container 4.1 through the bottom openings 4.1.1, the cutting holes 6.1, 8.1 and the sample container openings into the respective sample container 2.1.

To cut through the roots, not shown, the cutter 6 is guided along the cutting plate 8 in the direction of the arrow (stroke direction 10) so that the roots are sheared off between the cutter 6 and the cutting plate 8, i.e., at the edges of the cutting holes 6.1, 8.1. In order to enable the movement of the cutter 6 parallel to the stroke direction 10, the cutter 6 has longitudinal recesses 6.2 on both its long sides, which will be explained in more detail below. Furthermore, slot-like receptacles 6.3 are provided for actuating the cutter 6.

The cutting plate 8 on hand is designed as a removable cover 8 for the lower section 2, wherein the cutting plate 8 is releasably secured to the lower section 2 by means of first clamps 12. As is apparent in particular from FIGS. 1 and 5, the first clamps 12 embrace the lower section 2 and the cutting plate 8 in a clip-like manner and snap with locking projections 12.1 formed on the free ends of the first clamps 12 into correspondingly formed locking receptacles 8.2 of the cutting plate 8 and behind a locking collar 2.2 formed on the lower section 2.

In order for the first clamps 12 to not interfere with the movement of the cutter 6 along the cutting plate 8, the cutting plate 8 projects beyond the first clamps 12 in the assembly position of the lower section 2 and the cutting plate 8.

Further, the assembly, which is formed from the lower section 2 and cutting plate 8 attached thereto by means of the first clamps 12, is releasably connected to the cutter 6 and the upper section 4 by second clamps 14. For this purpose, the abovementioned components are precisely arranged one above the other and clamped by means of the second clamps 14. Analogous to the clamping connection between the lower section 2 and the cutting plate 8, the lower section 2 and the upper section 4 have locking receptacles 2.3 and 4.3, which in a position of use shown in FIGS. 4 to 6 enter a releasable locking connection with locking projections 14.1 formed at free ends of the second clamps 14.

To better guide the cutter 6 between the cutting plate 8 disposed on the lower section 2 and the upper section 4, sections of the base 4.2 of the upper section 4 facing the cutter 6 are formed level or planar as a cutter guide 4.2.

According to the first exemplary embodiment, the inventive sampling device is designed such that the cutter 6 can be moved in the stroke direction 10, relative to the cutting plate 8, despite the clamping connections formed by the first and second clamps 12, 14 between the upper section 4, the cutter 6, the cutting plate 8 and the lower section 2.

This is possible, inter alia, because longitudinal recesses 6.2 are formed on the two long sides of the cutter 6. Accordingly, a movement of the cutter 6 parallel to the arrow 10 and in the required range of movement is not hindered by the second clamps 14. A cutter stroke defined in the stroke direction 10 is limited by the length of the longitudinal recesses 6.2. The assignment of the cutting holes 6.1 of the cutter 6 to the cutting holes 8.1 of the cutting plate 8, the bottom openings 4.1.1, on the one hand, and the sample container openings on the other hand, is preferably chosen such that in a first stroke end position of the cutter 6, the cutting holes 6.1, 8.1 are superimposed such that during the development of the plants, the plants can grow unhindered from the cultivation container 4.1 into the sample container 2.1, and that the roots of the plants are severed in the second stroke end position. The severing of the roots takes place without contamination as long as the cutter stroke is selected to be smaller than a specified distance of adjacent cutting holes 6.1, 8.1 and/or sample containers 2.1 in the stroke direction 10 of the cutter 6.

Figure 7:
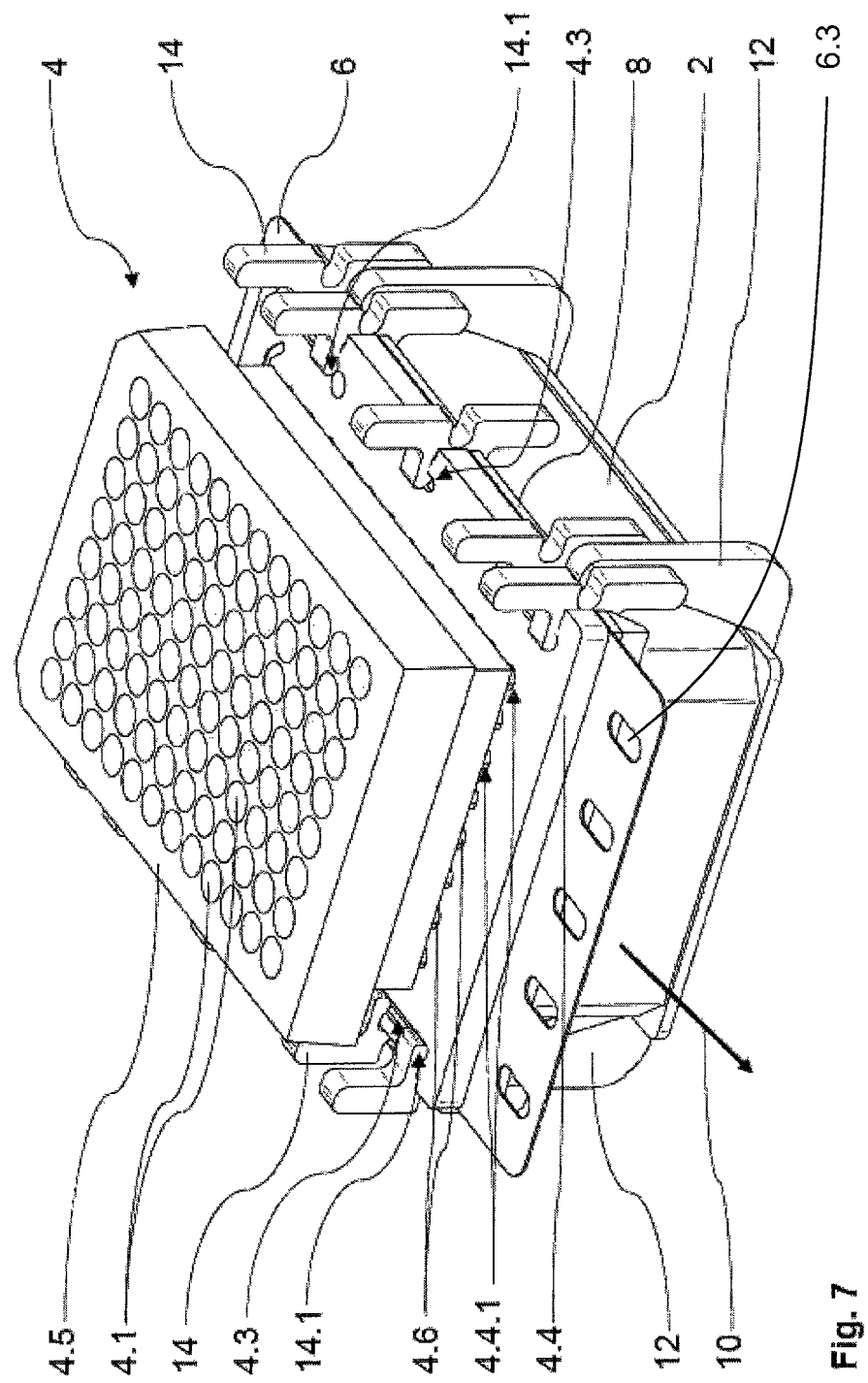
FIG. 7 illustrates an exemplary embodiment of the sampling device in a perspective assembly view corresponding to FIG. 4.

FIG. 7 shows a second exemplary embodiment of the sampling device according to the invention in an assembly position. In contrast to the first exemplary embodiment, the second exemplary embodiment has a two-part upper section 4. The upper section 4 here comprises a base plate 4.4 and an attachment 4.5 carrying the cultivation container 4.1, wherein the attachment 4.5 and the base plate 4.4 are releasably connected to one another in a position of use shown in FIG. 7.

The split of the upper section 4 serves to facilitate multiple use of the sampling device or to use the attachment 4.5 with the cultivation containers 4.1 as a pre-assembled part.

In the present exemplary embodiment, the bottom opening of each cultivation container 4.1 of the attachment 4.5 is surrounded on the outside by a tubular collar 4.6, wherein the collar 4.6 in the assembly position of the sampling device shown in FIG. 7 essentially extends as far as the end of the base plate 4.4 facing away from the attachment 4.5.

To secure the attachment 4.5 to the base plate 4.4, the attachment 4.5 is inserted with the tubular collar 4.6 into passage holes 4.4.1 formed on the base plate 4.4. The collars 4.6 and the corresponding passage holes 4.4.1 at the same time provide for positioning of the attachment 4.5 to the base plate 4.4.

The attachment 4.5 and the base plate 4.4 are preferably made of plastic.

In the position of use shown in FIG. 7, the assembly formed in this way of the base plate 4.4 and the attachment 4.5 comprising the cultivation containers 4.1 is releasably connected to the other components, namely the lower section 2 comprising the sample containers 2.1, the cutter 6 and the cutting plate 8, as already explained in regards to the first exemplary embodiment, by means of second clamps 14. Analogously to the first exemplary embodiment, the lower section 2 and the cutting plate 8 are also connected to each other in advance by means of first clamps 12.

FIGS. 8 to 11 details a third exemplary embodiment of the sampling device.

Figure 8:
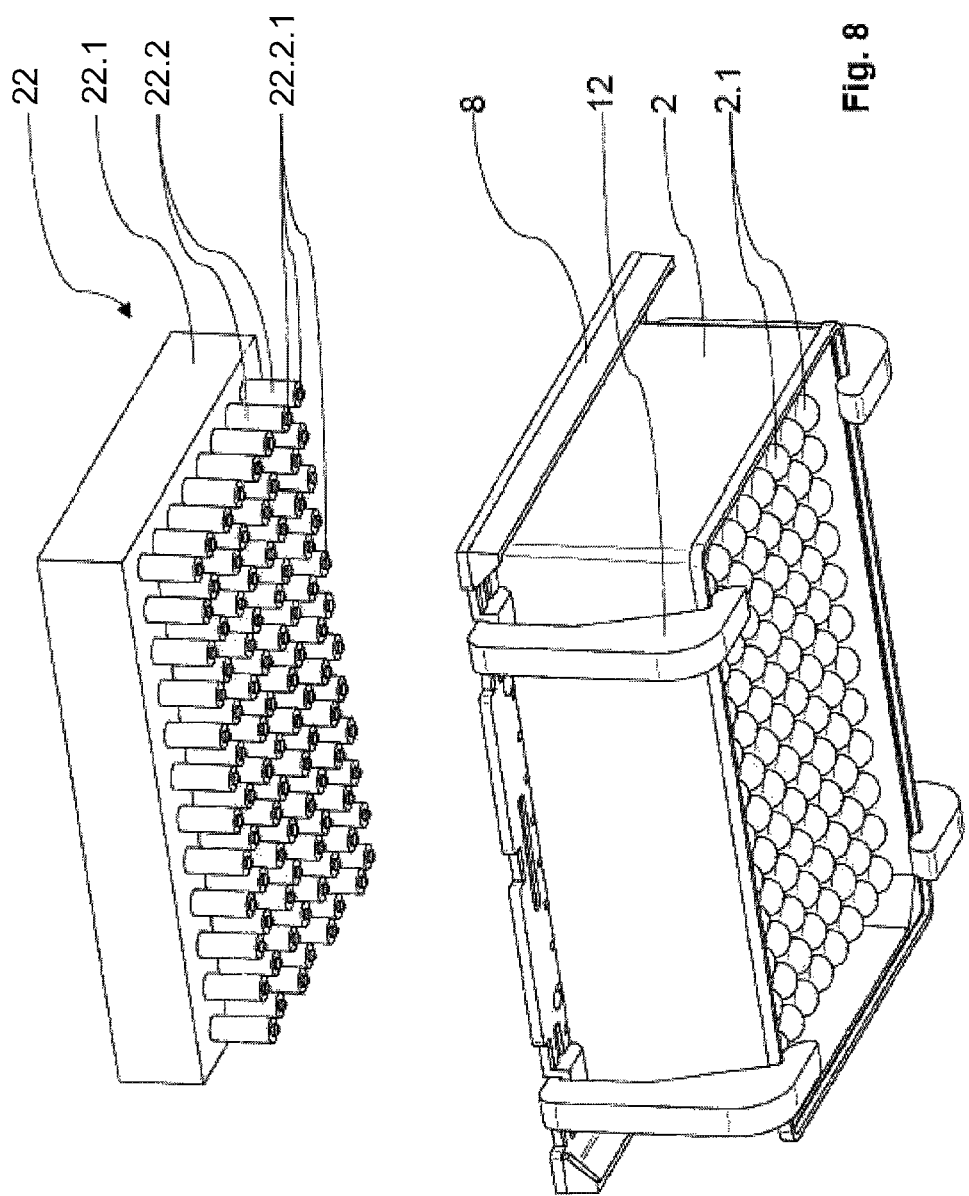
FIG. 8 illustrates an exemplary embodiment of the sampling device in a first perspective exploded view in a partial view.

FIG. 8 shows the third exemplary embodiment in an exploded perspective view in a partial view. Shown is the assembly of the lower section 2 with the sample containers 2.1, the first clamps 12 and the cutting plate 8. The lower section 2 with the sample containers 2.1 and the first clamps 12 as well as the components of the sampling device, not shown, such as the upper section 4 and the cutter 6, may be formed analogous to the first or the second exemplary embodiment.

The sampling device is presently additionally assigned a further component, namely a punch 22 of a punching device 20, which is not shown here and will be discussed in detail below. Pins 22.2 rise from a base plate 22.1 of the punch 22, each having a positioning head 22.2.1. The number of pins 22.2 is identical with the number of sample containers 2.1 and thus with the number of cultivation containers not shown here. The punch 22 is preferably made of a metallic material or plastic.

The punch 22 serves to reliably avoid cross contamination of the root samples when the cutting plate 8 is lifted off. For this purpose, after cutting the roots and removing the one-piece or two-piece upper section 4, not shown, the punch 22 punches out circular sections 8.5 from the cutting plate 8 around the individual cutting holes 8.1 and transfers these into the interior of the respectively assigned sample containers 2.1. There, they can also remain during subsequent laboratory testing.

Figure 9:
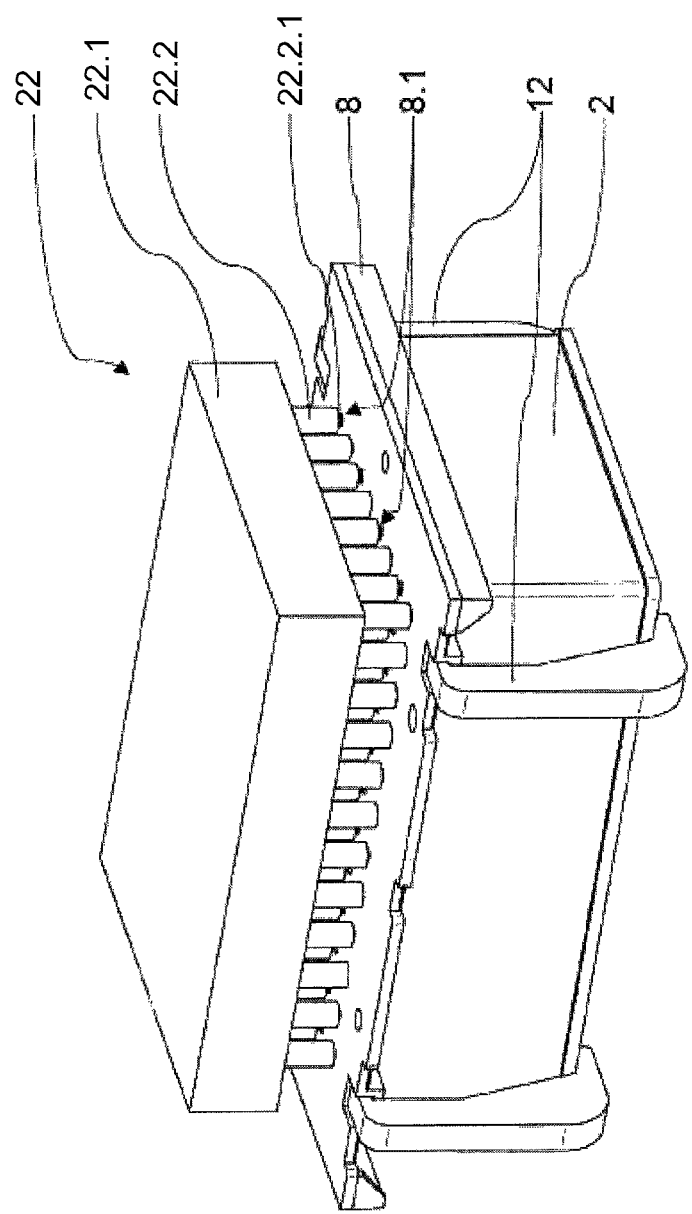
FIG. 9 illustrates the exemplary embodiment of the sampling device in a second perspective exploded view in a partial view.

As shown in FIG. 9, the punch 22 is brought into engagement with the cutting plate 8 for this purpose. In order to ensure and facilitate reliable alignment of the punch 22 with its pins 22.2 to the cutting plate 8 and the cutting holes 8.1, during the approach of the punch 22 to the cutting plate 8, initially the positioning heads 22.2.1 formed on the pins 22.2 are brought into engagement with the cutting holes

8.1 of the cutting plate 8. During the further movement of the punch 22 in the direction of the cutting plate 8, the pins 22.2 of the punch 22 come into contact with the edges of the cutting holes 8.1 of the cutting plate 8.

Figure 10:
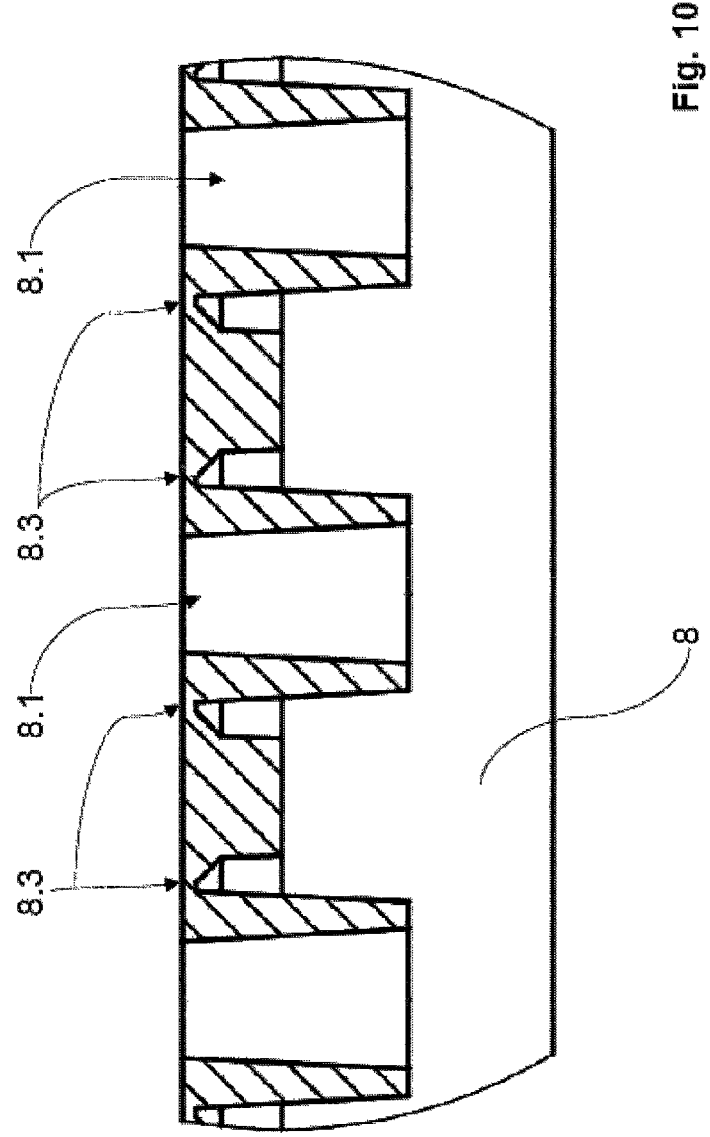
FIG. 10 illustrates the exemplary embodiment of the sampling device in a detailed view in the region of a cutting plate in a sectioned, partial view.

FIG. 10 shows a detail of the sampling device according to the third embodiment in the area of the cutting plate 8. Illustrated are the edges 8.3, which surround the cutting holes 8.1 of the cutting plate 8. The thickness of the cutting plate 8 is weakened at the edges 8.3, so that the punch 22, not shown here, breaks the predetermined breaking points of the cutting plate 8 thus formed in the further movement in the direction of the cutting plate 8. During movement in the direction of the cutting plate 8 in the image plane of FIG. 10, the punch 22 is lowered manually or driven by a motor from above onto the cutting plate 8.

Figure 11:
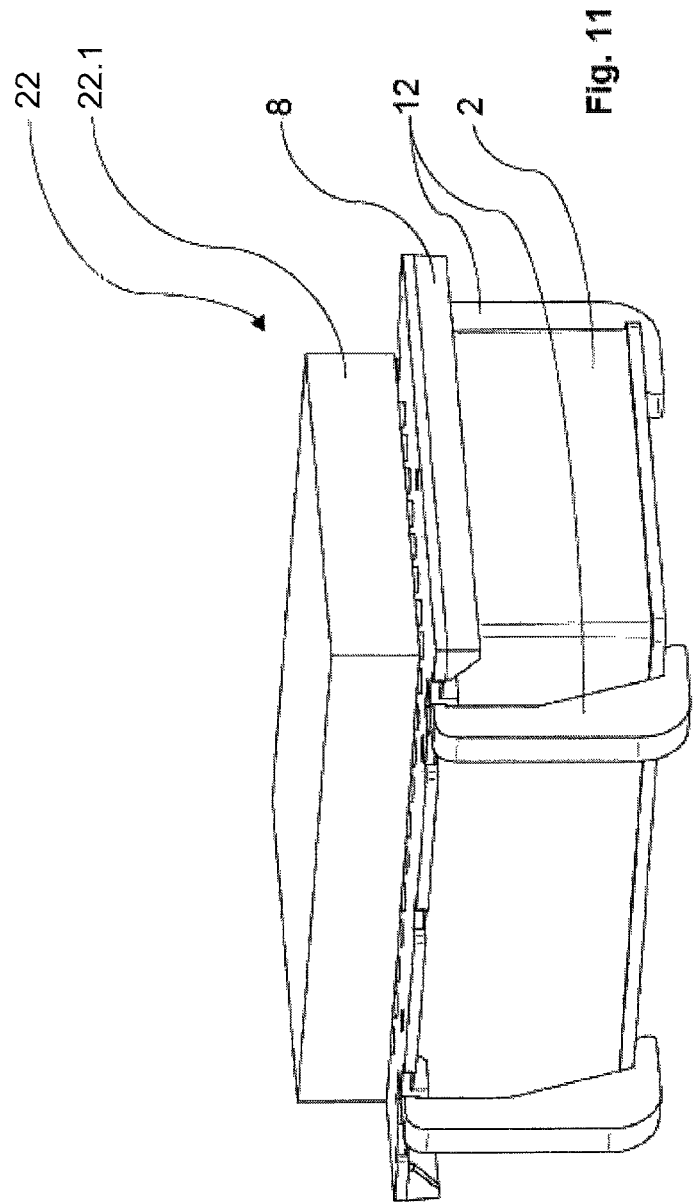
FIG. 11 illustrates the exemplary embodiment of the sampling device in a first perspective engagement view in a partial view.

The individual pins 22.2 of the punch 22, during the described movement of the punch 22, have a corresponding dimensioning to reliably transfer the edges 8.3 of the cutting plate 8 with the cutting holes 8.1 formed therein in the direction of the cutting plate 8 into the interior of the respective corresponding sample container 2.1, and to hold it in the sample container 2.1 in order to effectively prevent an undesired removal of root samples from the sample containers 2.1 during removal of the cutting plate 8 from the lower section 2 and thus from the sample containers 2.1. The lower section 2 and the sample containers 2.1 are also not shown in FIG. 10. FIG. 11 shows the punch 22 in the end position (actuating position), in which the punch 22 rests with its base plate 22.1 on the cutting plate 8 and is provided adjacent thereto. For the sake of clarity, the base plate 22.1 in FIG. 11 is shown not completely lowered to the cutting plate 8.

Figure 12:
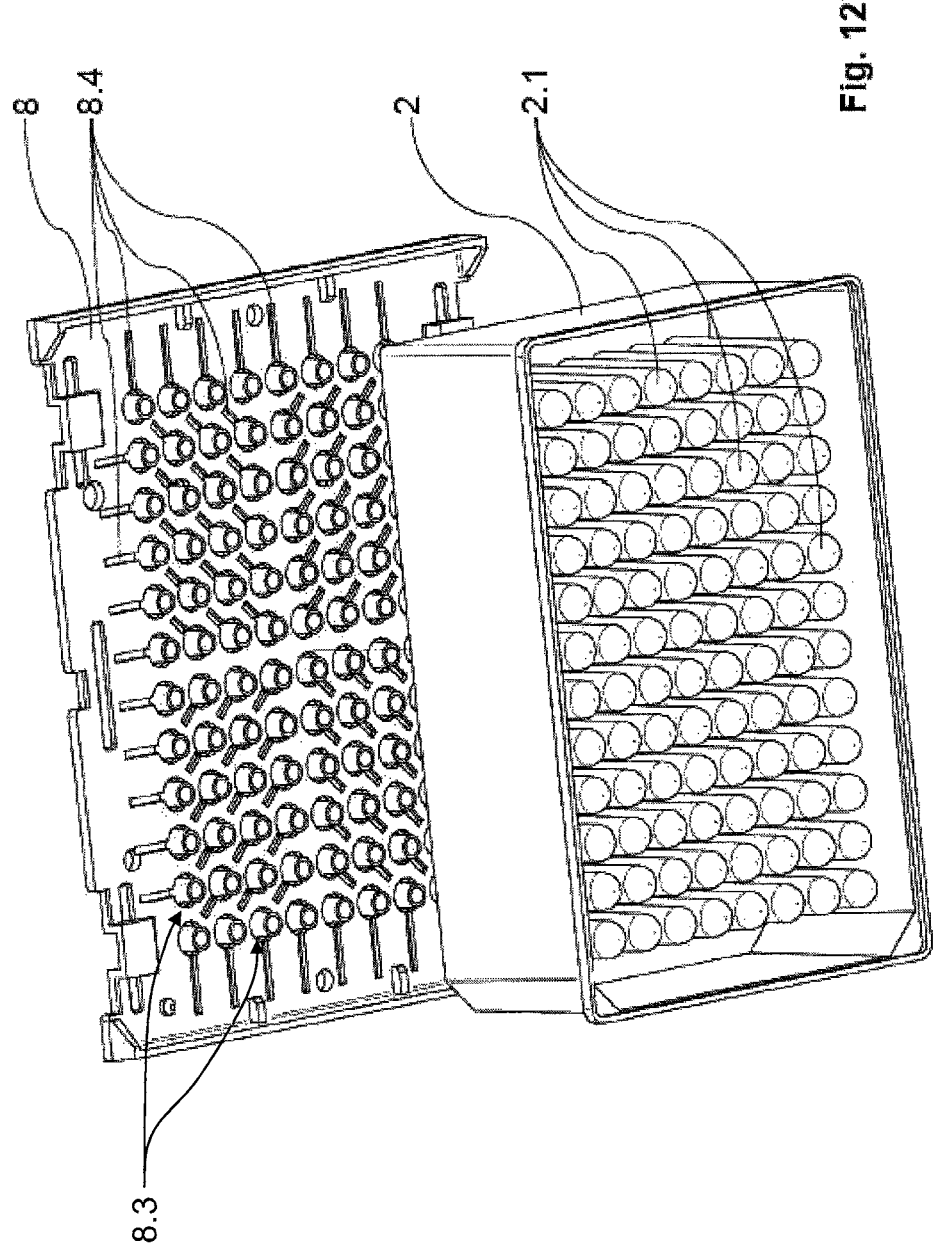
FIG. 12 illustrates an exemplary embodiment of the sampling device in a first perspective exploded view in a partial view.

FIG. 12 further shows a fourth exemplary embodiment. Shown is the lower section 2 with the sample containers 2.1 and the cutting plate 8 in a perspective bottom view. The lower section 2 with the sample containers 2.1 as well as the components of the sampling device, not shown, such as the upper section 4 and the cutter 6, may be formed analogously to the first or the second or the third exemplary embodiment.

In contrast to the already explained exemplary embodiments, the sampling device of the fourth exemplary embodiment has a modified cutting plate 8. As can be seen from FIG. 12, the edges 8.3 and drainage openings 8.4 designed as grooves are formed in the bottom of the cutting plate 8. In the assembly position of the lower section 2 and cutting plate 8, not shown, each of the drainage openings 8.4 is assigned to exactly one sample container 2.1, so as to effectively prevent unwanted cross contamination.

As already explained with reference to the first exemplary embodiment, plants are grown in the cultivation containers 4.1 not shown in FIG. 12. For this purpose, the cultivation containers 4.1 are filled with nutrients for plant growth. In order to store the required amount of water for growth, granules or the like may be added to the cultivation containers 4.1. The cultivation containers 4.1 are preferably watered from above, so as to soak the granules with water, which is then released from the granules to the plants. When watering, it may happen that an excess amount of water is supplied to the individual cultivation containers 4.1. This water cannot be absorbed by the granules; it runs through the bottom openings of the affected cultivation containers into the sample containers 2.1 assigned thereto.

For cultivation, it is desired and not harmful that there is water in the sample containers 2.1. However, it is not desired that the cultivation containers 4.1 are flooded with water. Therefore, in the fourth exemplary embodiment, a drainage opening 8.4 designed as a groove is provided for each sample container 2.1. The grooves 8.4 are arranged on the bottom of the cutting plate 8 such that water, which cannot be absorbed by the individual sample container 2.1, does not rise in an undesirable manner into the corresponding cultivation container 4.1, but rather passes through the sample container opening, not shown, into the respective groove 8.4 and can drain through the bottom of the cutting plate 8 without flowing into one of the other sample containers 2.1 in an undesirable manner. In this way, waterlogging is effectively avoided and the necessary gas exchange is guaranteed.

Figure 13:
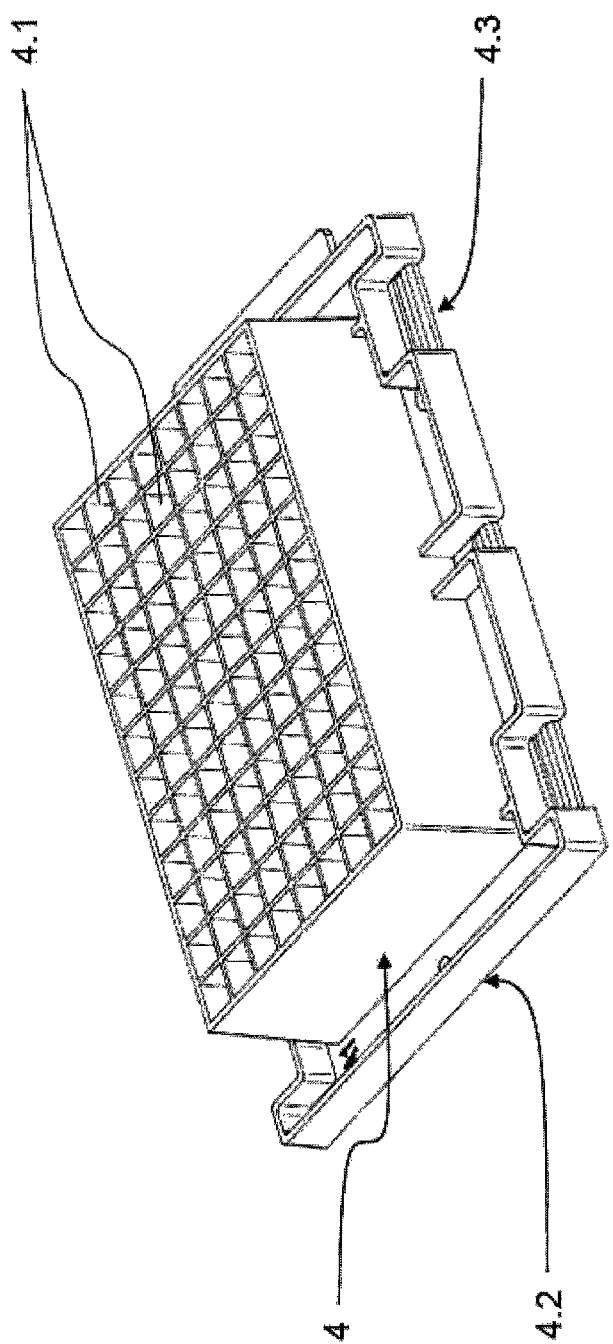
FIG. 13 illustrates an embodiment of the sampling device in a perspective exploded view in a partial view.
Figure 14:
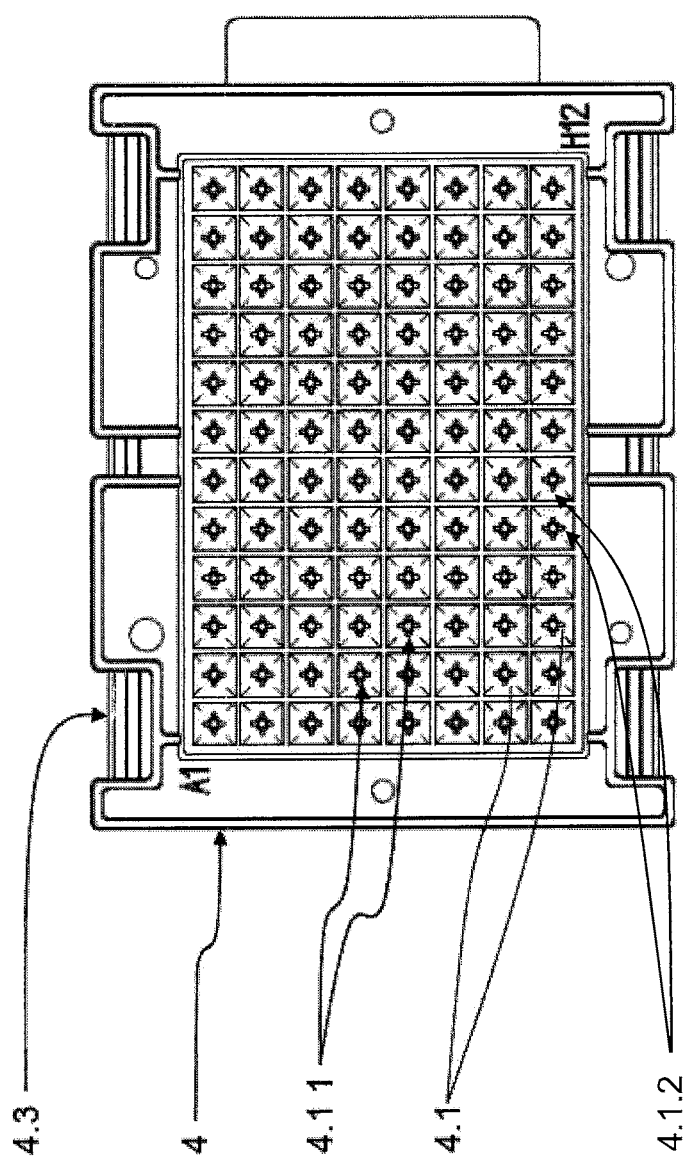
FIG. 14 illustrates the exemplary embodiment of the sampling device in a plan view in a partial view.

With reference to FIGS. 13 and 14, a fifth exemplary embodiment of the sampling device is detailed. FIG. 13 shows the fifth exemplary embodiment in a perspective exploded view in a partial view. Shown is the upper section 4 with the cultivation containers 4.1, which are provided in a 12×8 matrix-like arrangement. According to the fifth exemplary embodiment, unlike previously, the cultivation containers 4.1 are rectangular in cross section. The rectangular cross section of the cultivation containers 4.1 provides a very good use of space, i.e., with an unaltered size of the upper section 4, the volume of the cultivation containers 4.1 can be increased.

The bottom openings 4.1.1 provided on the upper section 4 for each cultivation container 4.1 are surrounded in the circumferential direction by a plurality of tabs 4.1.2 pointing away from the lower section 2 of the sampling device as seen in the assembly position. The tabs 4.1.2 are spaced and arranged such that a blockage or obstruction of the bottom opening 4.1.1 by the nutrients is counteracted and that at the same time it can be ensured that in the cultivation phase, the roots can develop into the lower section through the bottom openings 4.1.1.

Of course, the upper section 4 can also be formed in two parts in the rectangular embodiment of the cultivation container 4.1 according to the fifth exemplary embodiment. Analogous to the realization of the inventive sampling device according to FIG. 7, the upper section 4 then comprises the base plate 4.4 and the attachment 4.5 with the cultivation containers 4.1 that are rectangular in cross section.

For carrying out the method according to the invention, it is also possible to use other sampling devices other than the one shown.

In order to be able to reliably align the individual components of the sampling device, for example lower section 2, upper section 4, cutter 6 and cutting plate 8, with less of a burden in terms of monitoring, the components can have at least partially mutually corresponding positioners even if the upper section 4 is not split into two parts.

The positioning means may further be designed as coding, by which faulty mounting of the components of the sampling device is effectively prevented by simple means.

In the mentioned exemplary embodiments, the sample containers 2.1 of the lower section 2 and the cultivation containers 4.1 of the upper section 4 are each an integral part of the lower section 2 or the upper section 4 or of the attachment 4.5. However, this is not mandatory. For example, it can also be provided that the sample containers 2.1 and/or the cultivation containers 4.1 are at least partially formed as a separate component.

The sampling device can be designed for single use as well as for repeated use. While the first embodiment is more suitable as a disposable sampling device, the second embodiment is better suited for multiple use.

In contrast to the exemplary embodiments, it would be fundamentally conceivable that a cultivation container 4.1 with its bottom opening 4.1.1 does not necessarily correspond exactly to a sample container 2.1 and its sample container opening. It would also be possible for a cultivation container 4.1 with its bottom opening to be assigned to a plurality of sample containers 2.1 and their sample container openings. As a result, the same plant material can be submitted for different tests.

The cutter 6 does not necessarily have to be designed as a perforated plate. It is also conceivable that, for example, only the cutting plate 8 is formed as a perforated plate and the cutter 6 is suitably selected by the subject matter expert according to the individual case in respect of type, material, shape, dimensioning and arrangement.

For example, in addition to other suitable materials, cutters 6 made of hardened tool steel, alloyed tool steel, hard metal, plastic or even cutting ceramics are possible. The same applies to the material of the cutting plate 8.

In the two exemplary embodiments, in the assembly position of the sampling device, the second clamps 14 interact, inter alia, with locking receptacles 2.3 formed on the lower section 2. However, since the lower section 2 and the cutting plate 8 are releasably connected with each other by first clamps 12, it would also be conceivable that the second clamps 14 cooperate with locking receptacles 8.2 formed on the cutting plate 8.

The inventive cultivation and sampling method now provides, for example, that a plant is grown in the cultivation container 4.1. For this purpose, the substrate or the nutrients are added to the cultivation containers 4.1 of the upper section 4 of the sampling device, or the upper section 4 or the entire sampling device is provided pre-assembled with the substrate or nutrients already present herein and the seed is added to the cultivation containers 4.1.

After a cultivation phase, in which the plants develop and the roots of the plant grows into the corresponding sample containers 2.1 through the bottom opening 4.1.1 of the cultivation container 4.1, the cutting holes 6.1 of the cutter 6, the cutting holes 8.1 of the cutting plate 8 and the sample container openings, the root parts provided in the lower section 2 are separated from the plants with the cutter 6.

During a subsequent analysis phase, the lower section 2 of the sampling device with the root parts located therein is supplied to an analysis device. The upper section of the sampling device with the vital, i.e., intact and fully functional (remaining) plants can be further cultivated until the analysis results are available and/or pending selection. In the analysis device, phenotypic descriptions and/or molecular biological testing is performed on the root parts. After carrying out the analysis, it is determined which plants have particularly favorable, desired properties with regard to certain specification features. For example, this may be cold tolerance, pest resistance or the like.

After the corresponding plants have been identified, the upper section 4 of the sampling device is supplied to a selection device (see FIG. 25). The upper section 4 of the sampling device or the attachment 4.5 of the upper section 4 is positioned in a receptacle 31 of a signaler 30 of the selection device at a defined location. A cultivation container 4.1 of the sampling device is then optically identified by the signaler 30. For this purpose, the signaler 30 provides a light emitting diode array 32 which comprises a plurality of light emitting diodes, which are arranged corresponding to the cultivation containers 4.1 (see FIG. 26). Consequently, the plant having the particularly favorable properties is located in the identified cultivation container 4.1. At least a part of the plant present in the cultivation container 4.1 is then removed for further processing.

Figure 15:
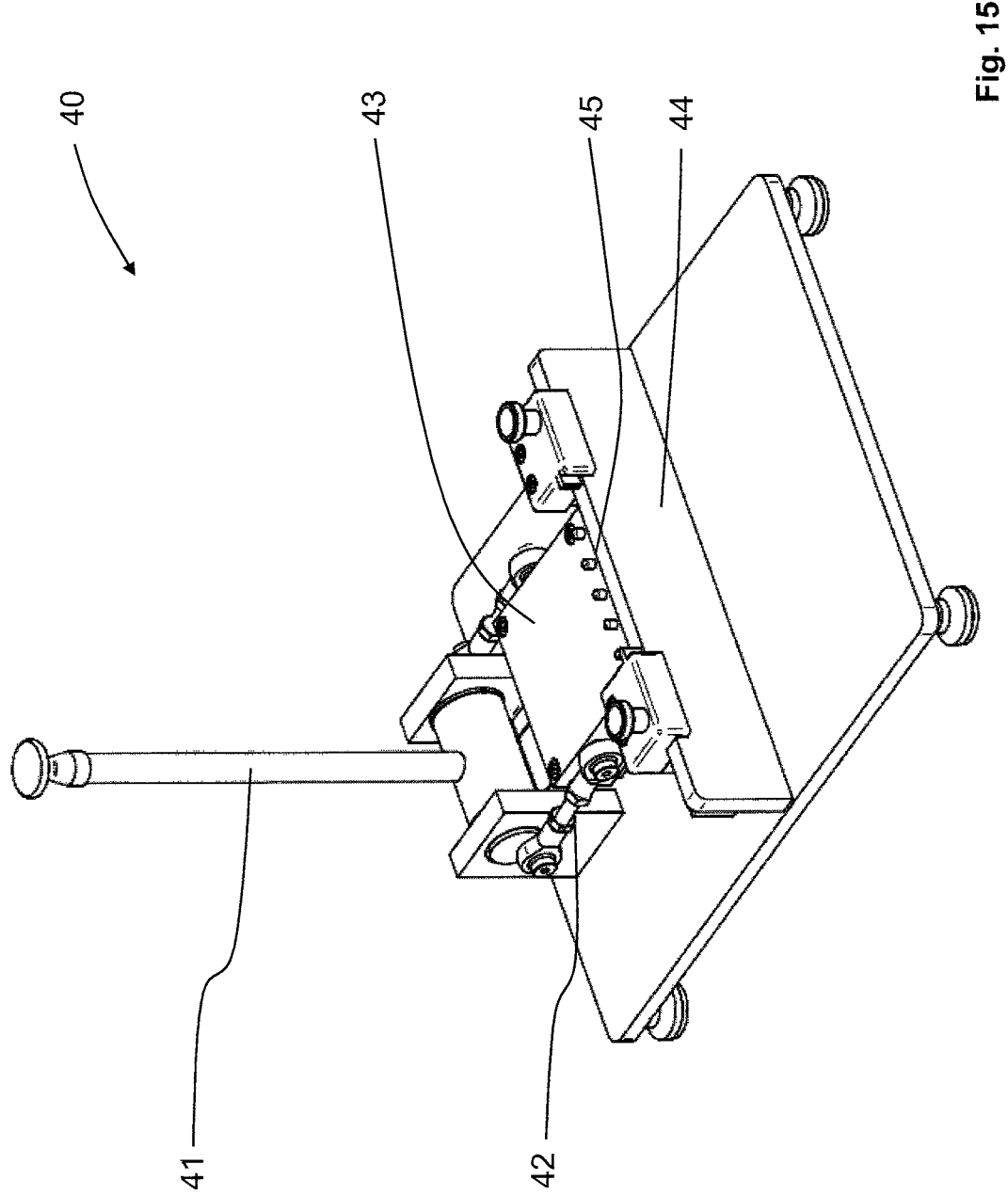
FIG. 15 illustrates a separating device used in carrying out the inventive cultivation and sampling method in a basic position in a perspective view.

In the context of the inventive cultivation and sampling method, for automatic or manual mechanical actuation of the cutter 6, a separating device 40 can be provided, which is shown in a perspective detailed view in FIG. 15. The separating device 40 provides an actuating lever 41 and a stroke section 43 linearly adjustable via an eccentric 42 connected to the actuating lever 41. The stroke section 43 is provided in a basic position of the separating device 40 shown in FIG. 15 in a defined, predetermined position relative to a contact surface 44 of the separating device 40.

Figure 16:
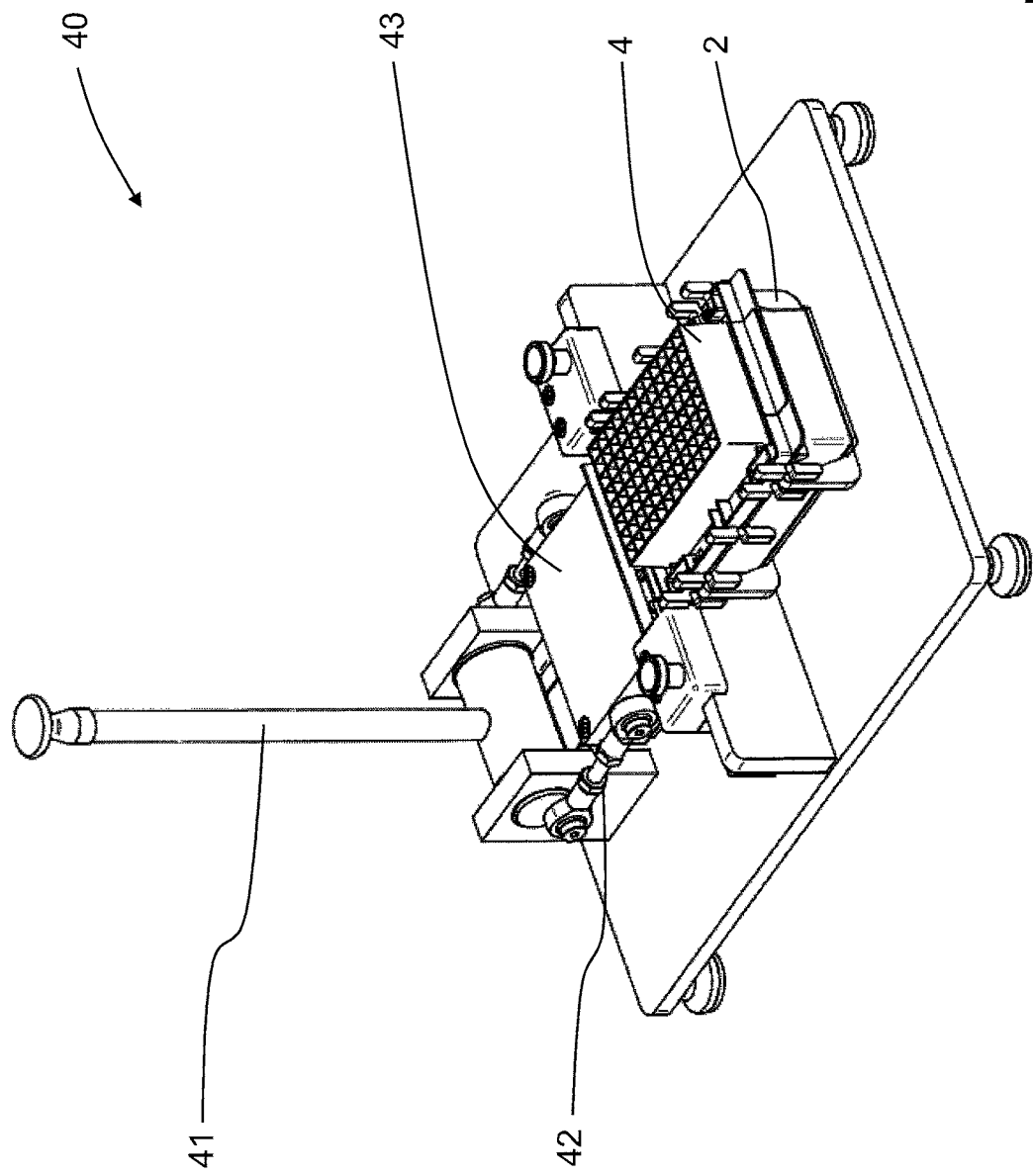
FIG. 16 illustrates the separating device according to FIG. 15 with the sampling device inserted therein in the basic position in the same perspective view.
Figure 17:
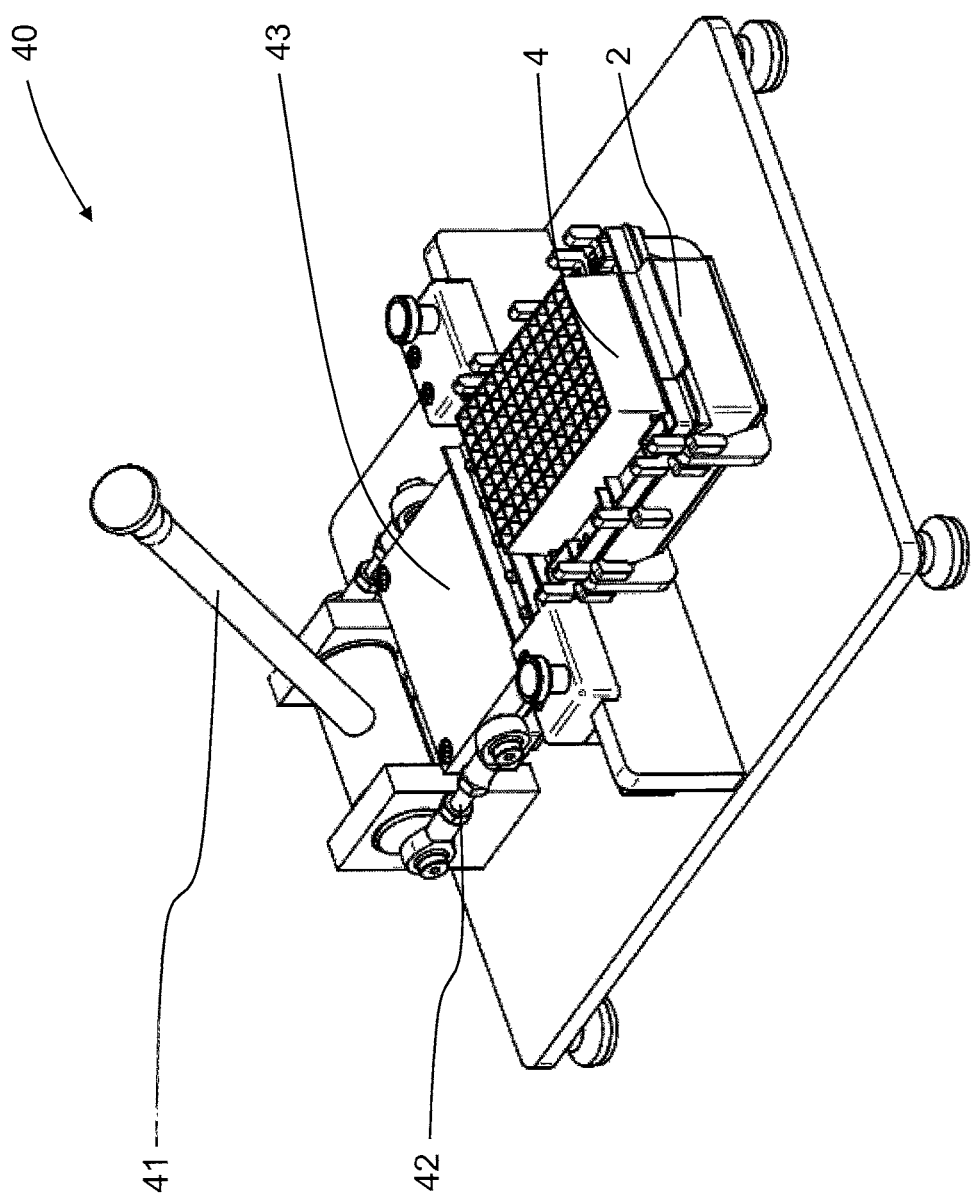
FIG. 17 illustrates the separating device with the sampling device in an actuating position.

FIGS. 16 and 17 show the separating device 40 with the sampling device inserted therein. It is in particular such that the sampling device is positioned against the contact surface 44 and the cutter 6 of the sampling device is connected to the stroke section 43 of the separating device 40. To this end, receiving pins 45 are provided on the stroke section 43, which engage in the receptacles 6.3 provided on the cutter 6. If the separating device 40 is now brought from the basic position into an actuating position by actuating the actuating lever 41, the cutter 6 of the sampling device is moved slowly in the stroke direction 10 and the roots of the plants are severed.

Figure 18:
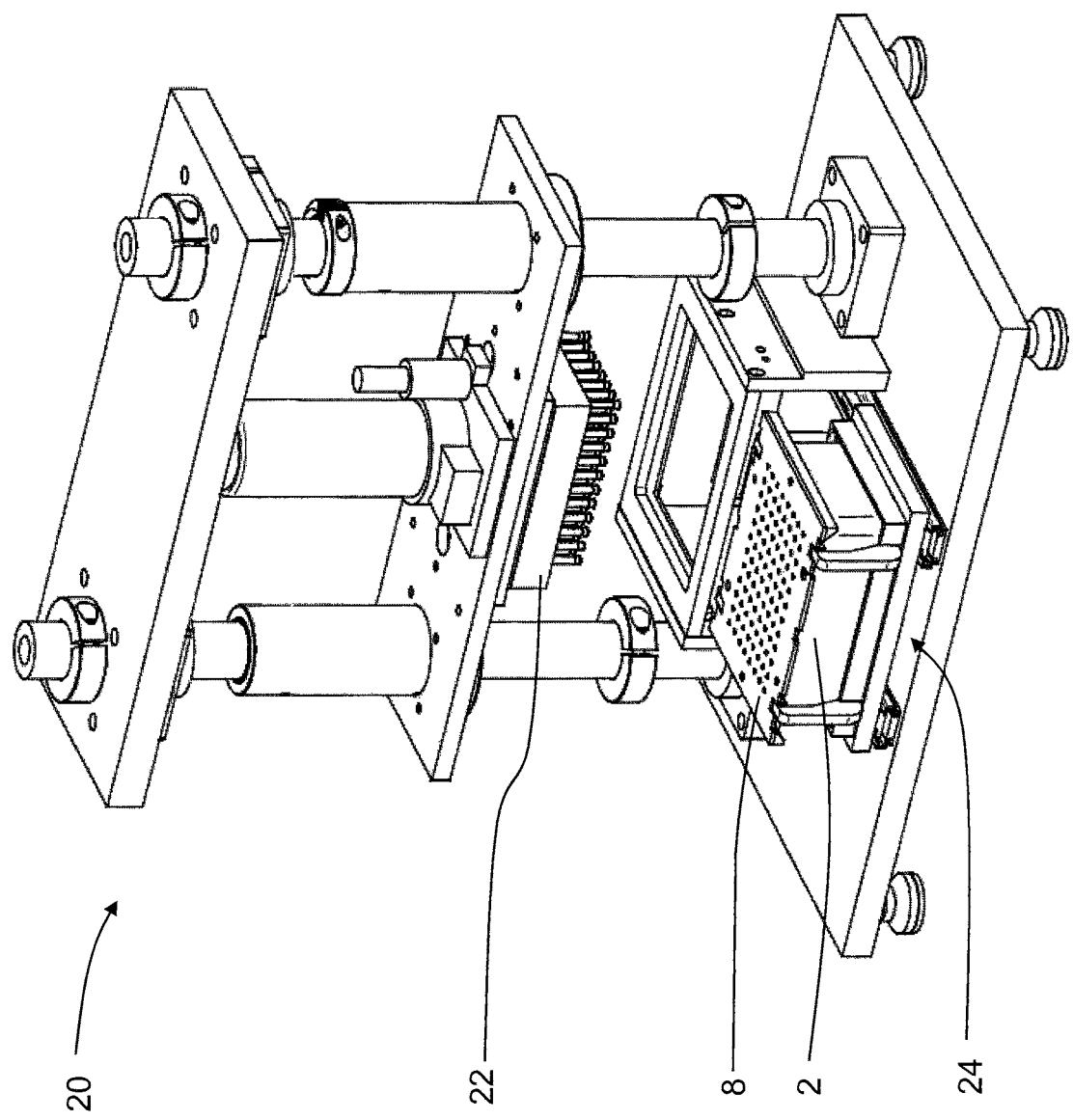
FIG. 18 illustrates a punching device used in carrying out the cultivation and sampling method according to the invention in a basic position.
Figure 19:
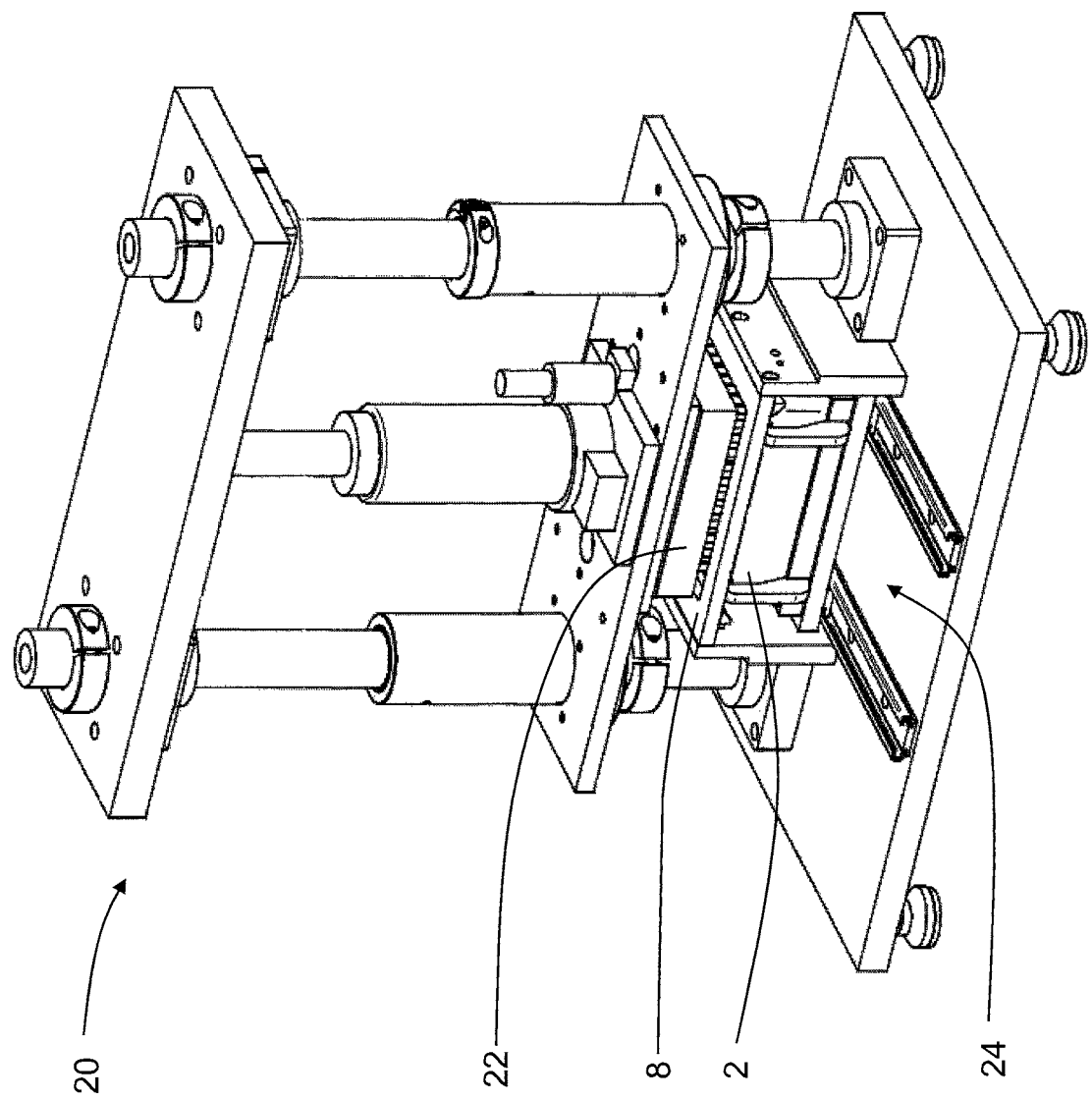
FIG. 19 illustrates the punching device according to FIG. 18 in an actuating position.
Figure 20:
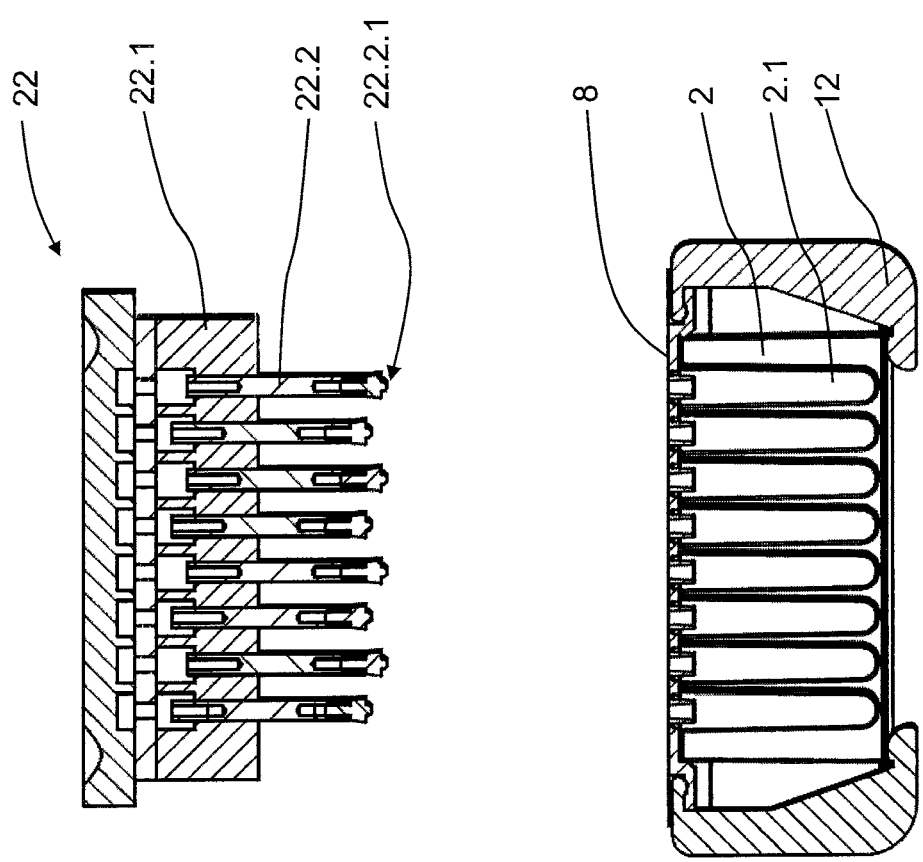
FIG. 20 illustrates a first step of a punching operation in a schematic diagram in section.
Figure 26:
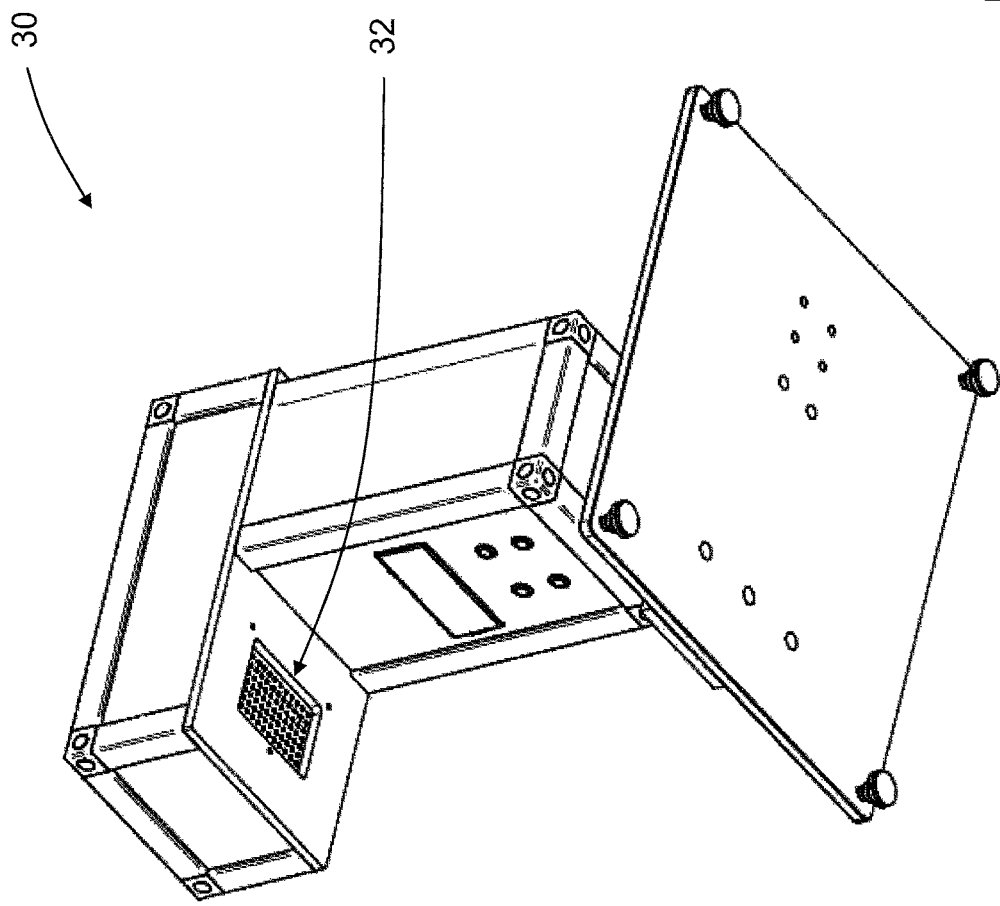
FIG. 26 illustrates the signaler of FIG. 25 in a second perspective view.

After cutting the roots, in preparation for the analysis of the plants, the lower section 2 of the sampling device, together with the cutting plate 8 fixed thereto, can be supplied to the punching device 20 shown in FIGS. 18 and 19. The punching device 20 includes the linearly displaceable punch 22 with the base plate 22.1 and the pins 22.2 and the positioning heads 22.2.1 provided on the pins 22.2. In addition, the punching device 20 comprises a receptacle 24, into which the lower section 2 of the sampling device can be inserted and moved longitudinally together with the cutting plate 8. The punch 22 of the punching device 20 is linearly actuated, for example by a motor, especially electromotively, or—as shown—pneumatically or hydraulically, and is brought from an upper basic position according to FIG. 18 into an actuating position after moving the sampling device below the punch 22.

The individual steps when punching are shown sequentially in FIGS. 20 to 24. According to FIG. 20, the punch 22 is provided in the upper basic position and the lower section 2, which is connected with the cutting plate 8 via the first clamps 12, is positioned below the punch 22. In addition, the punch 22 is lowered until at least first positioning heads 22.2.1 of the pins 22.2 engage in first cutting holes 8.1 of the cutting plate 8 (FIG. 21 and FIG. 10). If the stroke continues, first annular sections 8.5 are punched out of the cutting plate 8 by the first pins 22.2 and transferred into the associated sample containers 2.1, see FIG. 22. As a result, the other positioning heads 22.2.1 of the pins 22.2 are brought into engagement with the other cutting holes 8.1 of the cutting plate 8.

In a continuation of the punching movement, as shown in FIG. 23, the remaining annular sections 8.5 are punched out of the cutting plate 8 and transferred into the sample container 2.1. As soon as the punch 22 has assumed its lower basic position as shown in FIG. 24, the punching operation is completed. The root parts are in safe storage in the sample containers 2.1 together with the sections 8.5 and after raising the punch 22 out of the lower section 2, the cutting plate 8 can be removed from the lower section 2 of the sampling device after removal of the first clamps 12.

As part of laser-supported sowing of the plant seeds and/or laser-supported selection of the plants after analysis, a signaler 30 is used, which is shown in a perspective first representation in FIG. 25. The signaler 30 comprises a receptacle 31 for the upper section 4 or the attachment 4.5 of the upper section 4 of the sampling device. In addition, the signaler 30 includes a plurality of light emitting diodes, which are arranged opposite the receptacle 31 in a light emitting diode array 32 shown in FIG. 26. The light emitting diodes allow for the individual cultivation containers 4.1 of the upper section 4 to be optically identified during sowing and/or selection. The optical identification of the cultivation containers 4.1 is a guide for laboratory personnel and counteracts faulty sowing or harvesting.

For example, the inventive cultivation and sampling method takes place such that initially seed for the plants is added to the different cultivation containers 4.1 with the aid of a sowing device comprising the signaler 30. In this case, information is stored in a database as to which seed is stored in which cultivation container 4.1. In addition, an upper section identifier 4.7 of the upper section 4 and corresponding thereto, a lower section identifier 2.4 of the lower section 2 of the sampling device is stored.

In the cultivation phase, the plants are then developed. Cultivation takes place in a cultivation area, for example a greenhouse. It can preferably be provided that the plants are illuminated during cultivation with a special light of a light emitting diode lighting arrangement. It has been found that with appropriate illumination, the development of the roots can be promoted, and the growth of the plant shoots can be inhibited.

After sufficient development of the plants has taken place, the roots are severed by means of the separating device 40 and the lower section 2 together with the cutting plate 8 is fed to the punching device 20 for punching out the sections 8.5 from the cutting plate 8. After the removal of the cutting plate 8 from the lower section 2, the root parts provided in the lower section 2 are analyzed in an analysis device. For example, RNA and/or DNA analysis is performed on the root parts. The punched out sections 8.5 can remain in the sample containers 2.1 of the lower section 2 during this analysis.

After the analysis, plants are identified that strongly comply with a preferred specification for certain characteristics. In order to be able to carry out the further development with the corresponding plants, it is now necessary to select the particularly advantageous plants. Thus, the upper section 4, or the attachment 4.5 of the upper section 4 of the sampling device, is fed to a selection device and positioned. Furthermore, the upper section identifier 4.7 is recorded and optically identified by means of the signaler 30 of the cultivation container, in which the plant identified as being particularly advantageous is located. The plant can then be completely or partially removed. In particular, the plant itself can be repotted or transplanted. In the context of the inventive cultivation and sampling method, typically only the primary root is severed. Lateral roots can take on the function of the primary root, so that the plant can be immediately used for further cultivation.

According to an alternative embodiment of the method according to the invention, instead of the optical identification of the cultivation containers 4.1, the sowing or removal of the shoots can be automated or semi-automated at the time of sowing or selection or in addition to the identification. The sowing device and/or the selection device can provide a gripper for this purpose, which is preferably positioned automatically and then adds the seed to the selected cultivation container 4.1 or at least removes portions of the plant shoot from the cultivation container 4.1. For example, the gripper can be moved and positioned in two coordinates above the upper section 4 of the sampling device.

The inventive cultivation and sampling method can be provided continuously or partially automatically. For example, the various functional devices may be linked by control technology or data technology. In particular, continuous monitoring and identification throughout the entire process can be ensured by recording and/or storing and/or monitoring the seed identifier, the upper section identifier 4.7 of the sampling device and the lower section identifier 2.4 of the sampling device in the various method steps, and in particular by storing, which seeds are introduced into which cultivation container 4.1 of the sampling device, which roots have grown in which sample container 2.1 of the sampling device, which specification or which properties the plants have and which shoots can be selected and reused due to their particularly advantageous properties. For example, the sowing device, the separating device 40, the punching device 20 and/or the selection device may have a detector for the seed identifier, upper section identifier 4.7 and/or lower section identifier 2.4. Continuous detection and monitoring of the plants, plant parts or the sampling device is thus continuously ensured during the entire cultivation and sampling method according to the invention.

The invention being thus described, it will be obvious that the same may be varied in many ways. Such variations are not to be regarded as a departure from the spirit and scope of the invention, and all such modifications as would be obvious to one skilled in the art are to be included within the scope of the following claims

What is claimed is:

1. A cultivation and sampling method for plants grown in a multipart sampling device, wherein the sampling device provides an upper section with a number of cultivation containers, and a lower section with an equal number of sample containers, and wherein the upper section, in an assembly position of the sampling device, is connected to the lower section with the lower section being arranged underneath the upper section, such that each of the sample containers is aligned with and corresponds to each of the cultivation containers, the method comprising:
   during a cultivation phase, in the upper section of the sampling device, the plants are grown in the cultivation containers filled with a substrate and/or nutrients;
   separating the roots, provided in the lower section, from the plants with a cutter after the roots of the plants have grown through a bottom opening provided on each cultivation container into the sample container provided underneath the cultivation container in the assembly position of the sampling device;
   during an analysis phase, the lower section of the sampling device with the roots provided therein is supplied to an analysis device and a phenotypic description and/or molecular biological testing is performed on the roots; and
   during a selection phase, the upper section of the sampling device with the plants therein is supplied to a selection device and positioned,
   wherein the roots are separated from the plants by guiding the cutter along a cutting plate of the sampling device, the cutting plate being fixed on the lower section, and
   wherein, in a preparation phase preceding the analysis phase, the lower section with the root parts provided therein, together with the cutting plate, is separated from the upper section of the sampling device and then fed to a punching device, and wherein annular or circular sections are punched out of cutting plate around cutting holes of the cutting plate via a punch of the punching device and are transferred into the interior of each assigned sample container.

2. The cultivation and sampling method according to claim 1, wherein the cutter is provided as part of the sampling device and held in the assembly position on the lower section and/or the upper section.

3. The cultivation and sampling method according to claim 1, wherein in the assembly position, sample container openings of the sample containers facing the bottom openings of the cultivation containers are covered by the cutting plate, and wherein the cutting holes of the cutting plate are provided as passage openings for the roots of the plants which correspond to the position of the bottom openings and the sample container openings.

4. The cultivation and sampling method according to claim 3, wherein the cutter provided between the upper section and the lower section of the sampling device is formed in the manner of a perforated plate with a number of cutting holes, which during the cultivation phase are arranged corresponding to the cutting holes of the cutting plate such that the roots are adapted to grow into the sample containers, and wherein for cutting the roots, the cutter is mechanically guided by a predetermined stroke in a stroke direction along the cutting plate, and wherein the stroke is chosen to be larger than a diameter of the cutting holes provided on the cutting plate and the cutter, and chosen to be smaller than the distance of two sample containers adjacent in the stroke direction.

5. The cultivation and sampling method according to claim 1, wherein prior to punching out the sections from the cutting plate, a positioning head provided on one free end of the punch facing the cutting plate is brought into engagement with the cutting holes of the cutting plate to provide exact positioning of the cutting plate and of lower section of the sampling device with the punching device.

6. The cultivation and sampling method according to claim 1, wherein the sections for different sample containers are punched out from the cutting plate in two or more stages with a time delay.

7. The cultivation and sampling method according to claim 1, wherein after punching out the sections and/or before feeding the lower section to the analysis device, the cutting plate is removed from the lower section.

8. The cultivation and sampling method according to claim 1, wherein, in the selection phase, each cultivation container is identified by a signaler of the selection device.

9. The cultivation and sampling method according to claim 8, wherein the analysis device and/or a separating device formed for actuating the cutter and/or the selection device and/or the punching device and/or the signaler are coupled in terms of control technology and/or data technology in such a way that the upper section identifier and/or the lower section identifier are recorded and are linked with an analysis result of the molecular biological testing of the roots and with a clear assignment to one of the sample containers and the associated cultivation container.

10. The cultivation and sampling method according to claim 8, wherein the signaler of the selection device optically identifies the cultivation container and/or the sample container.

11. The cultivation and sampling method according to claim 1, wherein in the selection phase, the cultivation containers of a same upper section of the sampling device are sequentially identified by a signaler of the selection device.

12. The cultivation and sampling method according to claim 1, wherein the sampling device with the plants provided therein is illuminated during the cultivation phase by light emitting diodes.

13. The cultivation and sampling method according to claim 1, wherein the cultivation containers are filled with brick grit as the substrate and/or with the nutrients and are then watered from above during the cultivation phase.

14. The cultivation and sampling method according to claim 1, wherein the sample containers are configured in the lower section in a 96 deep-well plate format.

* * * * *